(12) United States Patent
Kusumoto

(10) Patent No.: US 11,382,566 B1
(45) Date of Patent: *Jul. 12, 2022

(54) LEAD PLACEMENT ASSISTED BY ELECTROPHYSIOLOGY MAPPING

(71) Applicant: Walter Kusumoto, Chico, CA (US)

(72) Inventor: Walter Kusumoto, Chico, CA (US)

(*) Notice: Subject to any disclaimer, the term of this patent is extended or adjusted under 35 U.S.C. 154(b) by 723 days.

This patent is subject to a terminal disclaimer.

(21) Appl. No.: 15/819,745

(22) Filed: Nov. 21, 2017

Related U.S. Application Data

(60) Provisional application No. 62/453,854, filed on Feb. 2, 2017, provisional application No. 62/424,863, filed on Nov. 21, 2016.

(51) Int. Cl.
| | |
|---|---|
| *A61B 5/00* | (2006.01) |
| *A61B 18/14* | (2006.01) |
| *A61B 34/20* | (2016.01) |

(52) U.S. Cl.
CPC ............ *A61B 5/6852* (2013.01); *A61B 5/686* (2013.01); *A61B 5/6851* (2013.01); *A61B 18/1492* (2013.01); *A61B 5/6848* (2013.01); *A61B 5/6886* (2013.01); *A61B 2034/2051* (2016.02); *A61B 2562/043* (2013.01)

(58) Field of Classification Search
CPC .............. A61B 5/6852; A61B 5/0073; A61B 2017/00053; A61B 34/20; A61B 18/1492
See application file for complete search history.

(56) References Cited

U.S. PATENT DOCUMENTS

| | | | |
|---|---|---|---|
| 5,250,033 A | * | 10/1993 | Evans ............... A61M 25/0668 604/160 |
| 5,405,376 A | | 4/1995 | Mulier |
| 6,165,164 A | | 12/2000 | Hill |
| 6,171,303 B1 | | 1/2001 | Ben-Haim |
| 6,206,874 B1 | | 3/2001 | Ubby |
| 6,319,375 B1 | | 11/2001 | Plicchi |
| 6,496,712 B1 | | 12/2002 | Dahl |
| 7,815,577 B2 | | 10/2010 | Krishnan |
| 7,917,216 B1 | | 3/2011 | Ryu |
| 8,010,186 B1 | | 8/2011 | Ryu |
| 8,050,739 B2 | | 11/2011 | Eck |
| 8,172,757 B2 | | 5/2012 | Jaffe |

(Continued)

*Primary Examiner* — Alyssa M Alter
(74) *Attorney, Agent, or Firm* — Heisler & Associates

(57) ABSTRACT

Cardiac interventional devices are fitted with sensors coupled to an electrophysiology (EP) mapping system. The sensors can be in the form of electrodes and/or magnetic field sensors which are placed strategically upon the interventional devices. The interventional devices can thus be visualized on the EP mapping display when the interventional devices are being routed through various pathways adjacent to the heart of a patient. The interventional devices can include sheaths, and especially two part sheaths with a base separate from a tube, which base can be separated from the tube at an interface. Other interventional devices include an exoskeleton attachable to a lead, needles, guide wires, dilators, J wires and luminal catheters. The sensors are located along the interventional devices, typically including a sensor at a distal tip, as well as along a length of the interventional device, proximal of the distal tip, and with known spacing to further allow the interventional device to be fully and accurately caused to appear on the EP mapping display.

11 Claims, 13 Drawing Sheets

(56) References Cited

U.S. PATENT DOCUMENTS

| | | |
|---|---|---|
| 8,285,364 B2 | 10/2012 | Barbagli |
| 8,287,531 B2 | 10/2012 | Mest |
| 8,326,419 B2 | 12/2012 | Rosenberg |
| 8,388,549 B2 | 3/2013 | Paul |
| 8,403,925 B2 | 3/2013 | Miller |
| 8,406,866 B2 | 3/2013 | Deno |
| 8,755,864 B2 | 6/2014 | Hauck |
| 8,825,144 B2 | 9/2014 | Starks |
| 10,973,436 B2 * | 4/2021 | Kusumoto ............ A61B 5/287 |
| 2006/0253032 A1 | 11/2006 | Altmann |
| 2007/0021648 A1 | 1/2007 | Lenker |
| 2008/0177138 A1 | 7/2008 | Courtney |
| 2008/0183072 A1 | 7/2008 | Robertson |
| 2009/0171196 A1 | 7/2009 | Olson |
| 2011/0087105 A1 | 4/2011 | Ridley |
| 2011/0087175 A1 | 4/2011 | Krishnan |
| 2011/0098564 A1 | 4/2011 | Larson |
| 2012/0172717 A1 | 7/2012 | Gonda |
| 2013/0241929 A1 | 9/2013 | Massarwa |
| 2014/0018792 A1 * | 1/2014 | Gang .................... A61B 34/73 606/41 |
| 2014/0148688 A1 | 5/2014 | Ludwin et al. |
| 2014/0257102 A1 | 9/2014 | Hossack |
| 2015/0289781 A1 | 10/2015 | Grunwald |

\* cited by examiner

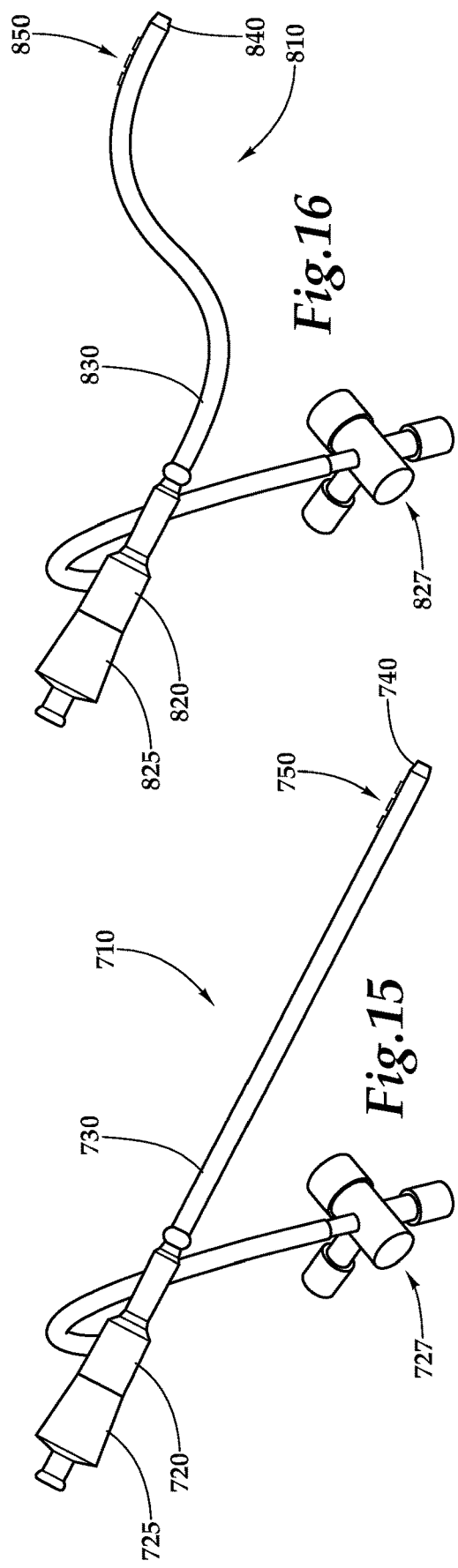
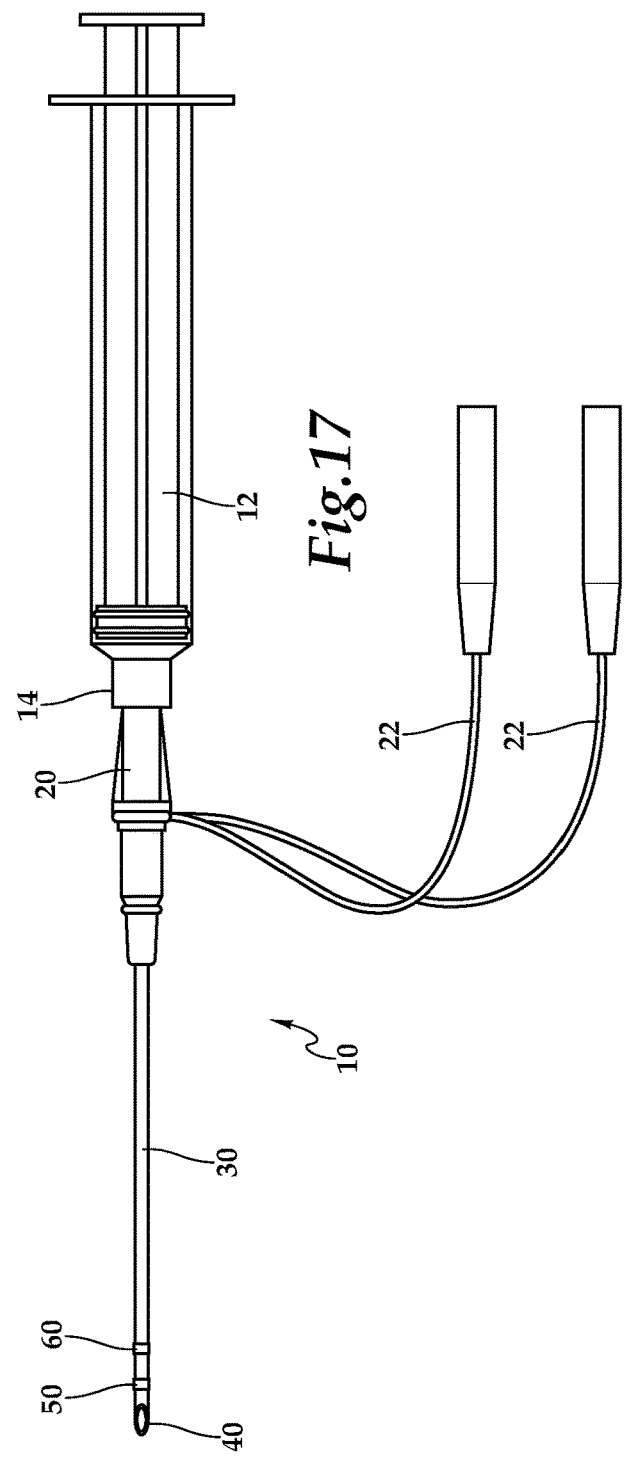

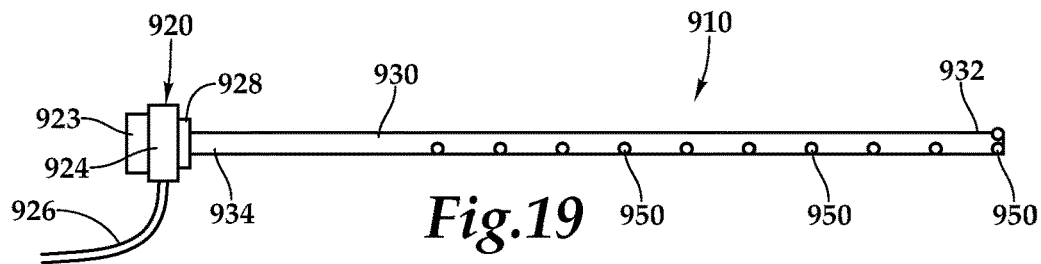
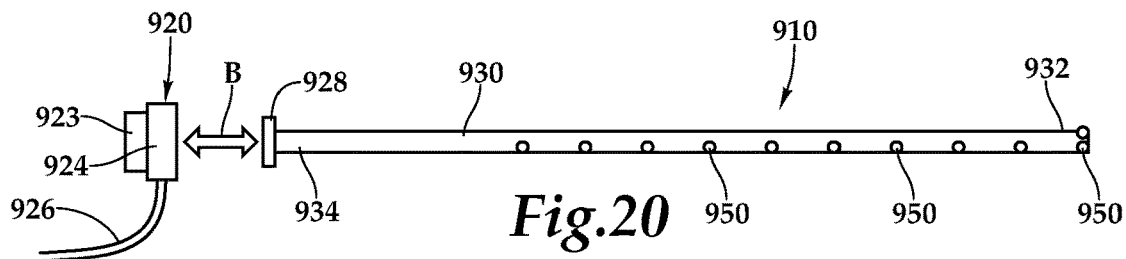
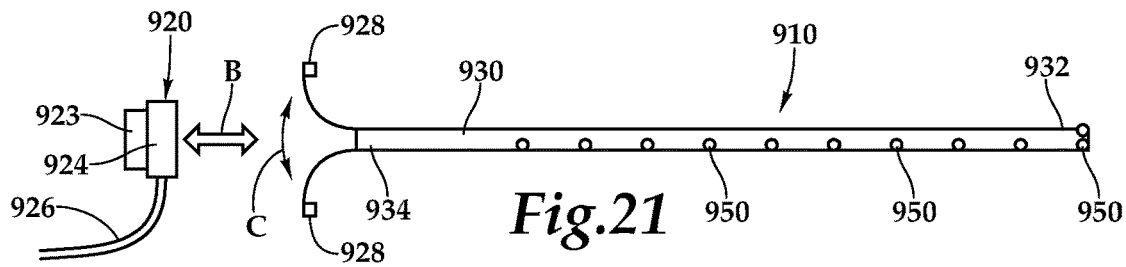
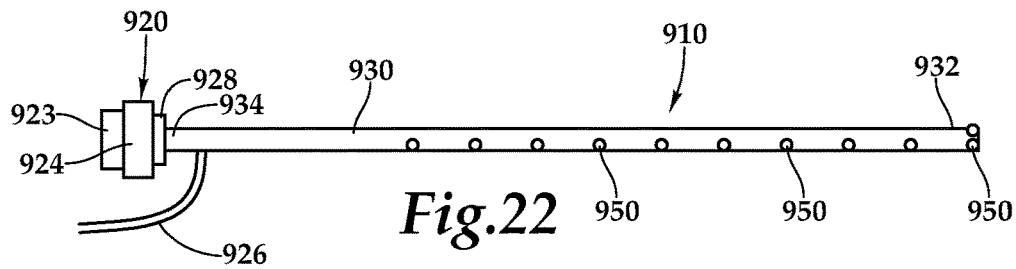
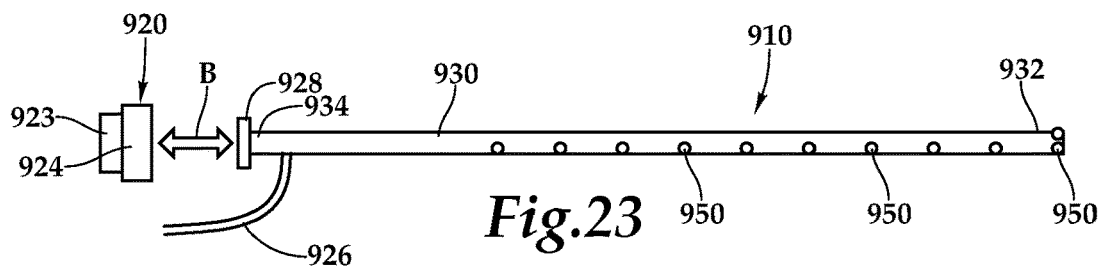
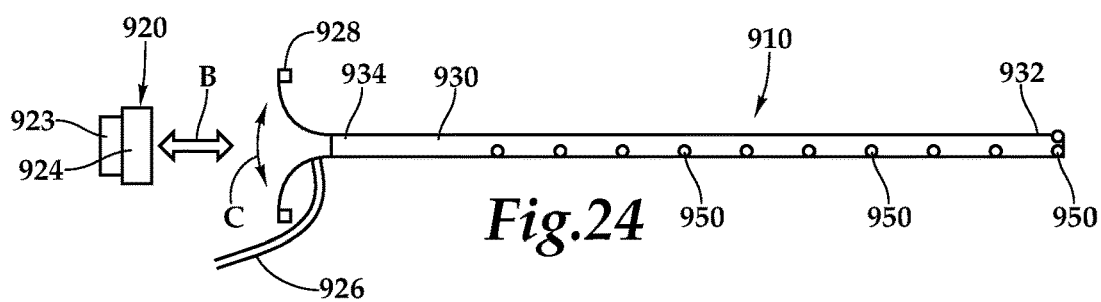

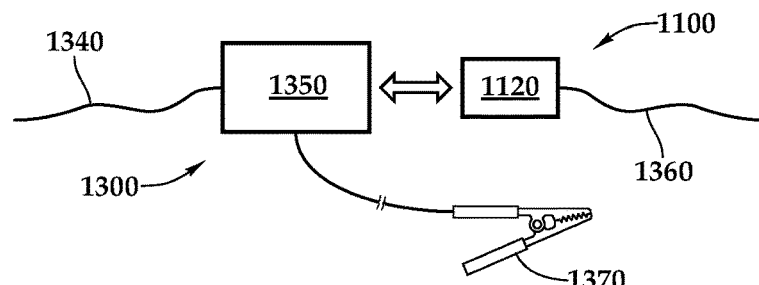
Fig.40
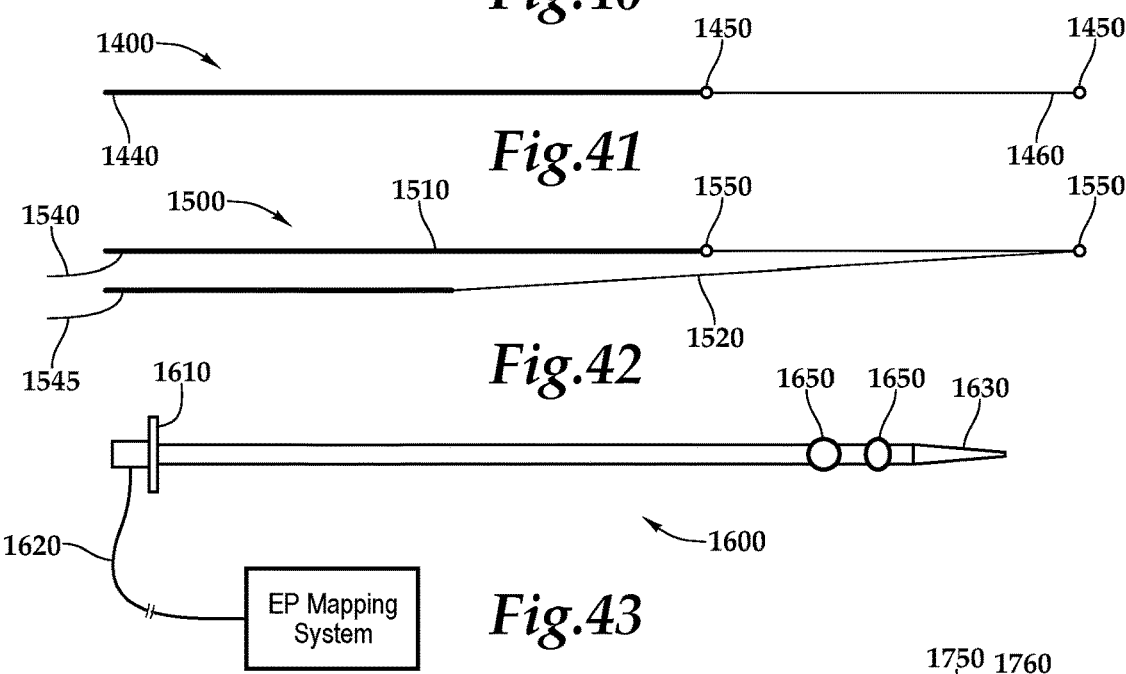
Fig.41
Fig.42
Fig.43
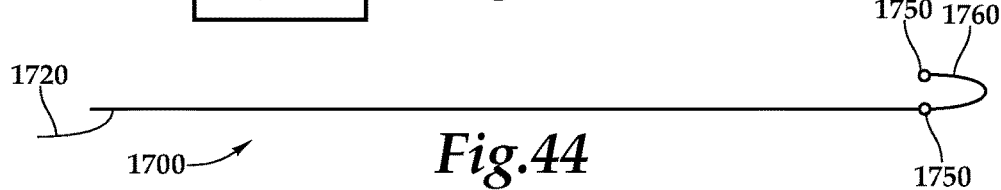
Fig.44
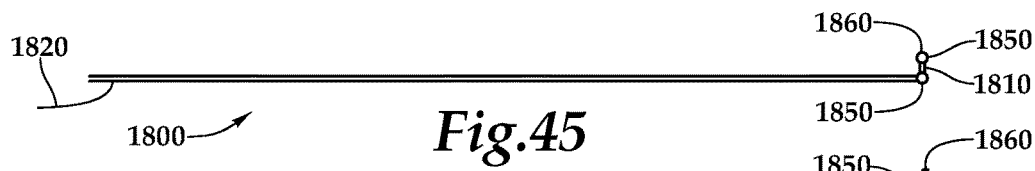
Fig.45
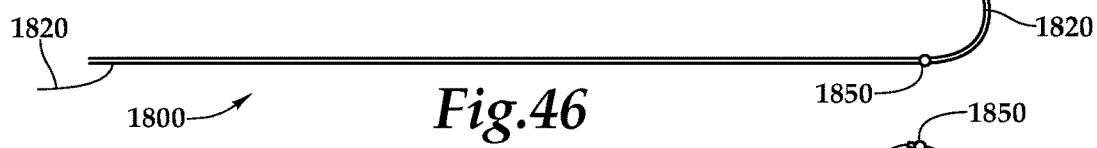
Fig.46
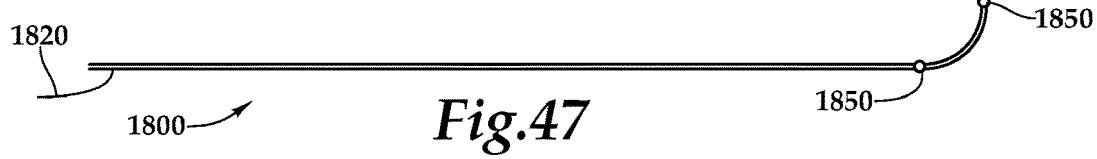
Fig.47

LEAD PLACEMENT ASSISTED BY ELECTROPHYSIOLOGY MAPPING

CROSS-REFERENCE TO RELATED APPLICATIONS

This application claims benefit under Title 35, United States Code § 119(e) of U.S. Provisional Application No. 62/424,863 filed on Nov. 21, 2016 and U.S. Provisional Application No. 62/453,854 filed on Feb. 2, 2017.

FIELD OF THE INVENTION

The following invention relates to lead placement tools when placing cardiac leads within or adjacent to particular desired portions of a heart of a patient. More particularly, this invention relates to interventional devices which include sensors thereon in the form of magnetic field sensors and/or electrodes, which are coupled to electrophysiology mapping (EP) systems, so that the EP mapping system can display the interventional device fitted with the sensors accurately upon a display of the EP mapping system.

BACKGROUND OF THE INVENTION

Pacemaker and implantable cardiac defibrillators have a central role in arrhythmia management worldwide. In 2009, over a million new implants occurred in the United States alone. Fluoroscopy is traditionally the accepted method of visualization of the leads for placement within the heart. However this exposes the patient, operator and staff members to radiation. Certain patient populations may be more vulnerable to radiation, such as pregnant patients or pediatric patients.

Radiation exposure during implantation is significant. The reference radiation dose in the placement of pacemakers and implantable cardiac defibrillators (ICDs) to the operator are 4 mSv (1.4-17 mSv). For cardiac resynchronization therapy (CRT) usually utilizing the coronary sinus, the radiation dose is 22 mSv (2.2-95). Doses of 10-100 milliSievert (mSv) correspond to a definite increase in life time risk of fatal and nonfatal cancers. For 10 mSv the risk is $\frac{1}{1000}$ and for 100 mSv the risk increases to $\frac{1}{100}$. Equally important to patient safety is operator and staff safety, and reducing radiation exposure is an important objective.

Cardiac electrophysiology(EP) mapping systems use intracardiac magnetic sensors and electrodes to localize the position of the heart. The Biosense Webster Carto 3, provided by Biosense Webster, Inc. of Diamond Bar, Calif., uses magnetic sensors within a magnetic field for positional information of catheters within the heart. This system also uses a background electric field utilizing current to localize electrodes on non-magnetic sensor EP catheters.

The EN SITE system provided by St. Jude Medical, Atrial Fibrillation Division, Inc. of St. Paul, Minn., uses impedance to localize various catheters relative to a stable catheter located within the heart. There is a background circuit utilizing a high frequency transthoracic electric field between the catheters and body surface electrodes, which detect impedance changes relative to a stable cardiac catheter (usually located within the coronary sinus) to derive location information within the heart. At the time of writing, St. Jude had developed a system that also employed a magnetic field, and was currently under FDA review.

Pacemakers and implantable cardiac defibrillators are a central pillar for arrhythmia management. Fluoroscopy is the primary method of visualizing placement of traditional intracardiac leads, and for emerging technologies such as leadless pacemaker systems. However, fluoroscopy exposes the patient, operator and staff members to significant radiation which can increase the risk of various health problems such as malignancy. Radiation exposure for placement of pacemakers, defibrillators and especially cardiac resynchronization therapy can be significant.

Many pacemaker, ICD and CRT implantation procedures occurs in the cardiac electrophysiology suite, where the cardiac EP mapping sits dormant. Thus, a need exists to use EP mapping systems to allow lead placement procedures to be performed in a highly reliable fashion with imaging guidance from the EP mapping system without exposure to radiation. Since the number of patients requiring this therapy is large, there is potential for broad applicability, and possibly cost savings as the patient volume can be leveraged to reduce the per unit cost of the proposed technology.

A complication of pacemakers/ICDs/CRT and leadless pacemakers is pericardial effusion and pericardial tamponade. A magnetic sensor or electrode mounted pericardiocentesis needle in conjunction with a cardiac EP mapping system to directly visualize entrance into the pericardial space can be readily available to avert catastrophe.

Permanent pacemaker/implantable cardiac defibrillators, cardiac resynchronization therapy and leadless pacemakers in conjunction with a cardiac electrophysiology mapping has the potential of reducing radiation exposure and increasing the precision of placement location of these permanent electrodes to increase safety for the patient, operator, and staff. This technology has broad applicability and the potential for wide spread adoption since the visual interface will be similar to current practices for operators.

SUMMARY OF THE INVENTION

With this invention, an interventional device is fitted with at least one, and preferably with a pair electrodes utilizing impedance and/or electrical current data or a magnetic sensor within a magnetic field to localize the device. In a first embodiment, the interventional device is depicted as a pericardiocentesis needle so that the needle tip can be visualized during pericardiocentesis or related procedures. This magnetic sensor or electrode in conjunction with existing cardiac electrophysiology mapping systems allows for direct/real time visualization of the entrance of the needle tip and dilator tip into the pericardial space. In addition, the cardiac electrophysiology mapping system can combine fluoroscopy, computer tomographic imaging and/or intravascular echo to further delineate epicardial/pericardial space and extracardiac structures during pericardiocentesis.

Electrophysiology mapping (hereafter EP mapping) systems are provided from multiple sources, and generally allow for an intra-vascular/intra-cardio catheter and/or electrode to have its location visualized within the heart. With this invention, a pericardiocentesis needle is outfitted in one of a variety of different manners, at least some of which are similar to the outfitting of catheters and/or electrodes within an EP mapping system which are placed intra-vascularly into or proximate to the interior of the heart. The pericardiocentesis needle is thus modified from prior pericardiocentesis needles to include at least one electrode thereon or some other sensor, such as a magnetic field sensor. This sensor, such as an electrode, is routed into the EP mapping system, such as in the same way that other electrodes or other sensors within an EP mapping system are integrated into the EP mapping system, such as the way that catheters and intra-venus electrodes of EP mapping systems are connected into such EP mapping systems for visualization thereof on a display of the the EP mapping system. One such EP mapping system is disclosed in U.S. Pat. No. 8,825,144, incorporated herein by reference in its entirety.

The methodology implemented by this mapping system is based on the principle that when electrical current is applied across two surface electrodes, a voltage gradient is created along the axis between the electrodes. Although any suitable number of electrodes may be utilized, typically six surface electrodes are placed on the body of the patient and in three pairs: anterior to posterior, left to right lateral, and superior (neck) to inferior (left leg). The three electrode pairs form three orthogonal axes (X-Y-Z), with the patient's heart being at least generally at the center.

These six surface electrodes are connected to the EP mapping system. In embodiments, such as those working with the St. Jude ENSITE EP mapping system, the various electrodes alternately send an electrical signal through each pair of surface electrodes to create a voltage gradient along each of the three axes, forming a transthoracic electrical field. Conventional electrophysiology catheters may be connected to the system and advanced to the patient's heart. As a catheter enters the transthoracic field, each catheter electrode senses voltage, timed to the creation of the gradient along each axis. Using the sensed voltages compared to the voltage gradient on all three axes, the three-dimensional position of each catheter electrode is calculated. The calculated position for the various electrodes can occur simultaneously and be repeated many times per second.

The EP mapping system can display the located electrodes as catheter bodies with real-time navigation. By tracking the position of the various catheters, the system provides non-fluoroscopic navigation, mapping, and creation of chamber models that are highly detailed and that have very accurate geometries. In the latter regard, the physician sweeps an appropriate catheter electrode across the heart chamber to outline the structures by relaying the signals to the computer system that then generates the 3-D model. This 3-D model may be utilized for any appropriate purpose, for instance to help the physician guide an ablation catheter to a heart location where treatment is desired.

In order to generate an accurate and highly detailed map of a patient's heart, a large amount of data is required. Accordingly, an electrode catheter may be swept across various surfaces of the heart while obtaining data as described above. In order to accelerate this mapping data acquisition and/or increase the volume of data available for mapping, a number of high-density electrode catheters have been developed or proposed. Generally, these include a number of electrodes in an array in relation to a catheter body so as to substantially simultaneously obtain many mapping data points for a corresponding surface of cardiac tissue proximate to the catheter body. For example, these electrodes may be deployed along the length of a section of the catheter body that has a coil or other three-dimensional configuration so as to provide the desired spatial distribution of the electrodes. Alternatively, the electrodes may be disposed on a number of structural elements extending from a catheter body, e.g., in the form of a basket or a number of fingers.

Once the mapping data has been acquired, software may be implemented to generate multiple surface images, which when combined, comprise a three-dimensional image of the patient's heart. This image can be displayed on a suitable output device in real-time so that the physician can "see" the patient's heart and the catheter for properly positioning the catheter at a work site within the patient's heart for a medical procedure (e.g., an ablation procedure).

The electrode or other sensor on the needle causes the location of the electrode relative to adjacent cardiac structures to be visualized on the display of the EP mapping system. By placing the electrode on the needle a known distance from a tip of the needle, and by knowing the orientation of the needle, the precise location of the tip of the needle can be known and visualized on the EP mapping system display. Knowing orientation of the needle can occur by having multiple electrodes on the needle, one distal and one proximal, so that the orientation of the needle is merely a line segment between the position of the two electrodes, or can be ascertained in some other fashion, such as by having a needle orientation sensor placed on the needle itself or other sensor physically attached to the needle. In one embodiment one of the electrodes can be the tip of the needle itself. By visualizing on the display the location of the tip of the pericardiocentesis needle in real time, a surgeon or other medical professional can precisely place the tip of the pericardiocentesis needle where desired relative to adjacent cardiac structures.

In certain environments, other imaging systems can be incorporated along with the EP mapping system, such as CT scans, MRI scans, ultrasound, fluoroscopy, etc. While the invention is described above in particular with regard to pericardiocentesis needles, other interventional devices have a transcutaneous nature can similarly be outfitted with electrodes or other sensors and integrated into the EP mapping system for visualization of location (and preferably also orientation) of such other devices. Such other devices include dilators, sheaths, catheters, stylets associated with needles and dilators, and other transcutaneous interventional devices. When EP mapping systems are referenced, these can be electric field based or magnetic field based, as described above (or some combination thereof).

In addition to needles such as pericardiocentesis needles, other interventional devices, especially for cardiac lead placement procedures are proposed, utilizing cardiac electrophysiology (EP) mapping systems to minimize radiation exposure, in conjunction with the various cardiac interventional devices. Such devices include sheaths and other lead placement devices mounted with magnetic field sensors or electrode sensors, while also optionally utilizing the electrodes of the pacemaker or implantable cardiac defibrillator (ICD) leads. As described above with this invention, and in a prior invention by the inventor herein, magnetic sensors or electrode sensors mounted on paricardiocentesis needles are disclosed in pending U.S. patent application Ser. No. 15/713,307, filed on Sep. 22, 2017, incorporated herein by reference in its entirety, and also with associated disclosure and drawings thereof included herein for convenience.

Other interventional devices, such as J-wires (or other navigation/guide wires), dilators or sheaths, can be similarly fitted with sensors, such as magnetic field sensors or electrodes to assist with the placement of cardiac leads and allow visualization of these instruments in a cardiac EP mapping system. Cardiac resynchronization therapy (CRT) can use catheters and sub-vessel selecting catheters mounted with magnetic sensors or electrode sensors as well. Shapeable coronary sinus wires equipped with electrodes and possibly magnetic sensors can sub-select branches of the coronary sinus. Leadless pacemakers can also be placed using catheters mounted with electrodes or magnetic sensors according to this invention.

As an option, these leads can be placed with a fluoroscopic or chest X-ray back drop utilizing landmarks for alignment with a cardiac EP mapping system. This will allow for a familiar visual experience for the cardiac electrophysiologist or cardiologist. Additional modalities utilizing echocardiography and/or CT scans can also be visualized on the cardiac EP mapping system. The cardiac EP mapping system allows for the combining of all or some of these imaging modalities which potentially allow for more precision in localization of lead placement within the cardiac chambers.

An electrode mounted coronary sinus wire can be visualized on an impedance and/or current based cardiac EP system. Leadless pacemakers are an emerging technology, and the electrodes of the leadless system are visualized by a cardiac EP mapping system. With this invention, the catheters and systems that place these leadless pacemakers are mounted with magnetic sensors or electrodes to allow for visualization of the catheter or non-catheter system in a cardiac EP mapping system. Electrode mounted catheters or systems can utilize impedance or current to visualize the catheter, which is then separately visualized from the leadless pacemaker electrodes.

In one design according to this invention, a sheath is mounted with a magnetic sensor and multiple electrodes to allow for visualization of the sheath as a surrogate for markers for the pacemaker/ICD lead in the EP mapping system. The lead enters the fastener, passes throught the sheath base, tear away base and sheath body, until the distal tip is at a fixed distance past the sheath tip. The fastener is locked down onto the lead. An example of a fastener can be a rotating mechanism to reduce the aperature around the lead. A sliding mechanism or a locking switch using a cam mechanism could also be used. The sheath body would be quite flexible, especially towards the tip. The flexibility would ideally be similar to the pacing/ICD lead, yet relatively strong longitudinually. There can be differential flexibility, where the sheath body towards the tear away base could be relatively stiffer compared to the distal end which would be quite flexible. A magnetic sensor (or electrode) could be at the tip, with electrodes (or magnetic field sensors) along the body of the sheath, which would allow visualization of the distal portion of the lead within the EP mapping system. One option is to provide ten electrodes, but any number of electrodes could be utilized. Also, multiple magnetic sensors along the sheath body could be utilized. The electrodes and/or magnetic sensors could also be distributed on both sides of the sheath.

The fastener would lock the lead in place. There could be a detection mechanism for the lead relative to the sheath, to warn the operator that the sheath and lead need to be resecured. In this design, the sheath base, and fastener with cable can be detached. Once the lead is in the desired location, and deployed, the fastener can be loosened, and the sheath base/faster can be removed from the body of the sheath. This can be a plug mechanism, twisting mechanism or switch with quick release or any combination thereof.

The tear away base of the sheath can be broken and the sheath body (i.e. the tube) can be removed. Electrodes and magnetic sensor(s) could be on a specific side of the sheath to allow for the sheath to be easily torn away. If necessary, a commercially available cutter tool could be used to secure the lead and cut away the sheath body. The sheath can be perforated, or have a rail system to tear away or guide the cutter throught the sheath. Alternatively a long stylet could be within the lead, and the entire sheath mechanism is removed in a proximal direction, while forward pressure is placed on the long stylet. This latter option for removal, would likely be more awkard for the operator and less desirable.

In another design, the electrode or magnetic sensor mounted sheath prototype has ten electrodes on a tube portion thereof, and a stop cock is optional. The silicone tube could be engineered as thin as possible to have a close fit with the lead. The flexibility could be similar to the pacemaker lead, and could also have differential flexibility along the length of the sheath. For example, the distal portion could be quite flexible, while the proximal portion could be less flexible. A pacing lead is inserted into the sheath. The sheath would be thinner, and can have similar pliability to a pacing lead, or have variable flexibility along the length of the lead. A 10 pin cable provides connection to the cardiac EP mapping system. After placement, the fastener to the pacemaker lead is loosened and removed from the lead and electrode and/or magnetie sensor mounted sheath tube.

In another embodiment, the sheath is an exoskeleton of electrodes and/or magnetics sensors that fit around the lead. the electrodes or magnetic sensors can fit on the spine or along the secondary attachements or splines which would fit around the lead. Once the lead is in place, the exoskeleton of electrodes and/or magnetic sensors can be removed from the patient. The secondary attachements or splines can be flexible and when removed to run parallel with the primary spine, thus potentially decreasing the diameter needed to place the lead. In this design, the electrodes or magnetic sensors could spiral around the cardiac pacing or implantable cardiac defibrillator lead.

Optionally, a secondary spine can be attached to the secondary attachments or splines which connect the pacemaker lead to the primary spine. The secondary spine is pushed/pulled to disattach the exoskeleton from the lead. after placement of the lead where desired, the exoskeleton of leads/magnetics sensors is removed from the patient, leaving the lead in place. The secondary attachements or splines can be flexible to straighten on removal from the patient.

As another option, there would be extra secondary attachements or splines throught the length of the exoskeleton. A secondary spine could also be added to this version. In this version the lead lock of the exoskeleton to the cardiac lead may be optional based on how efficient the secondary attachments or splines attach to the lead without movement between the cardiac lead and electrodes/and or magnetic senosors.

The electrodes or magnetic sensors could be located anywhere along the secondary attachments or splines, or both prongs of the secondary attachements or splines. A secondary spine can be provided for easy disattachment of the secondarary attachments or spines from the pacemaker lead. As one option, ten electrodes and/or magnetic sensors are provided at common spacing away from a distal tip.

As another variation, the exoskeleton can fit around the pacing/ICD lead, and have mounted electrodes and/or magnetic sensors. The exoskeleton can be a series of small wires, that fit around the pacing lead or ICD lead.

As another variation, the electrodes or magnetic sensors are placed upon a jacket that has a slot opening down the jacket of one side. The pacing lead or ICD lead fits into the jacket through this slot and locked in place by the fastener. The lead can later be displaced out of this slot and out of the jacket for removal of the exoskeleton in this variation.

Other interventional devices used in lead placement according to this invention include stylets mounted with magnetic sensors, J wires equipped with a magnetic sensor or electrode(s), coronary sinus wires equipped with magnetic sensors, sheaths, dilators and luminal catheters equipped with electrode(s) or magnetic sensors to deliver permanent pacemaker leads, implantable cardiac defibrillator leads, coronary sinus leads or leadless pacemaker systems into the heart, with visualization through a cardiac EP mapping system.

For instance, a stylet is equipped with magnetic sensor(s) which fit into a pacemaker or implantable cardiac defibrillator lead. Stylets will go through IS-1 or IS-4 ports through the body of the lead. The diameter of the lumen is typically set by industry standard between the different pacemaker/defibrillator companies. A magnetic sensor could be placed at the tip, and possibly another sensor or sensors (electrode or magnetic) within the body of the stylet. The tensile properties should be similar to current stylets, which are bendable, yet firm enough to hold a shape. The wires for the magnetic sensor could be braided together to increase the strength of the stylet. A very small amount of stiff insulation could also be used. Ideally no insulation with the exception of around the magnetic sensor could be used to maintain a similar tactile experience to the operator. Since multiple stylets may be used in a single implant, they should be relatively disposable Also provided in one form of this invention is an interface cable between the EP mapping system and the magnetic sensor mounted stylet/permanent pacemaker. The interface cable connects to the magnetic sensor stylet, and is easily attachable or detachable, so that other stylets can be utilized. This can be a male/female connection. The interface cable can have alligator clip(s) or other clip(s) to easily attach to the pacing electrodes on the permanent pacemaker/implantable cardiac defibrillator lead. The interface cable then connects to the EP mapping system. The interface cable could potentially be resterilized.

Another interventional device according to an embodiment of this invention is, a magnetic sensor or electrode mounted on a thin filament wire, composed of 2 wires which are relatively flexible and still hold a shape if bent by the operator, or can be preshaped to navigate branch vessels within the coronary sinus. Another magnetic sensor or electrode could be at the tip of the thicker wire body, and the wire body would go through the permanent pacemaker lead and back to the interface cable. This wire can be steered by the operator to a branch vessel of the coronary sinus. As a variation on such a navigation wire, a magnetic sensor(s) double wire can be provided for coronary sinus navigation. In such a design, a double wire is utilized. The main wire travels adjacent to the left ventricular lead while the secondary wire is within the lumen of the left ventricular lead. The main wire houses the magnetic (or electrode) sensors, while the secondary wire is very thin except at the opposite end which is stiffer to allow for back loading into the left ventricular lead. The entire double wire is then moved as a single unit to cannulate the desired coronary sinus branch. Once cannulated, the left ventricular lead is advanced over the secondary wire similar to a "buddy wire" technique. The thicker portion of the secondary wire is cut by the operator at the proximal end of the lead, and the main wire body is removed from the patient, along with the very thin secondary wire from the lumen of the left ventricular lead. This design allows for less space constraints for the magnetic sensor(s) or electrodes.

As another interventional device, a plastic dilator can be provided which has a wire which feeds to the distal tip electrode which is tapered, or can be located just proximal to the distal tip, so that a J wire would not interfere with the electrical properties of the electrode. Rather than electrodes, magnetic sensors could be located near the tip, to convey location within the magnetic field, and to confirm the presence of the dilator within the vascular space.

As a further interventional device according to this invention, a J wire mounted with magnetic sensors or electrode(s) is provided to allow for visualization of access within the intravascular space. In such a design, a J wire is equipped with either a magnetic sensor or electrode to allow for visualization within the intravascular system on a cardiac EP mapping system. It is likely a magnetic based cardiac EP mapping system would utilize a magnetic sensor whereas an electrical impedance or current based system would utilize an electrode(s). The J wire could have one or more electrodes or magnetic sensors thereon.

As a still further interventional device according to this invention, luminal catheters with magnetic sensors or electrodes can be visualized with the cardiac EP mapping system to visualize the tip of the catheter within a coronary space, such as the coronary sinus. Such luminal catheters are equipped with electrodes and/or magnetic sensors that can go through a sheath, and be visualized in a cardiac EP mapping system. The luminal catheters can have various shapes to sub-select a branch of the coronary sinus. These luminal catheters could accommodate a pacing lead and magnetic sensor mounted wire to be inserted into the selected branch of the coronary sinus. The catheter can be larger, to accommodate a "leadless" pacemaker so that this device could be delivered using a cardiac EP mapping system.

OBJECTS OF THE INVENTION

Accordingly, a primary object of the present invention is to provide a permanent cardiac pacing/implantable defibrillator/coronary sinus lead or leadless cardiac pacemaker lead utilizing a cardiac electrophysiology (EP) mapping system to reduce or eliminate fluoroscopy during implantation.

Another object of the present invention is to provide a pacing/implantable defibrillator/coronary sinus stylet equipped with a magnetic sensor(s) or electrode(s) on the tip and/or along the body to be visualized in a cardiac EP mapping system.

Another object of the present invention is to provide an interface wire between the stylet and the cardiac electrophysiology mapping system equipped with an additional electrical connector for the permanent pacemaker/defibrillator/coronary sinus lead proximal and distal electrodes.

Another object of the present invention is to provide a wire for navigation within the vascular tree and coronary sinus utilizing magnetic sensors or electrodes for a cardiac EP mapping system.

Another object of the present invention is to provide a dilator/sheath equipped with electrodes or magnetic sensor to deliver pacing/defibrillator leads which can be visualized in a cardiac EP mapping system.

Another object of the present invention is to provide a dilator/sheath/catheter equipped with electrodes or magnetic sensor to deliver a "leadless" pacemaker using a cardiac EP mapping system.

Another object of the present invention is to provide a J wire mounted with a magnetic sensor or electrode to allow visualization in a cardiac EP mapping system.

Another object of the present invention is to provide an electrode mounted coronary sinus wire or cardiac interventional wire, dilator, sheath and coronary sinus catheter which can utilize either impedance or current to give locational information for the cardiac electrophysiology mapping system.

Other further objects of the present invention will become apparent from a careful reading of the included drawing figures, the claims and detailed description of the invention.

BRIEF DESCRIPTION OF THE DRAWINGS

FIG. 15 is a perspective view of a sheath assembly with magnetic field sensors shown thereon as one form of sensors for visualizing a location of a tip of the sheath assembly according to one embodiment of this invention.

FIG. 16 is a perspective view of that which is shown in FIG. 15, but for a sheath having a curving contour.

FIG. 17 is a front elevation view of a variation of the needle of FIG. 3 with a syringe attached to a hub of the needle and with leads extending from the hub for interfacing into an EP mapping system.

FIG. 19 is a front elevation view of a sheath according to one embodiment of this invention, fitted with sensors and coupled to the EP mapping system of FIG. 18.

FIG. 20 is a front elevation view similar to that which is shown in FIG. 19, but after separation of a tube portion of the sheath from a base portion of the sheath.

FIG. 21 is a front elevation view of that which is shown in FIGS. 19 and 20, and further showing how at least portions of the tube can be cut away after lead placement, for removal thereof.

FIG. 22 is a front elevation view of a sheath similar to FIG. 19, but with the interconnection to the EP mapping system occurring through the tube of the sheath, rather than through the base of the sheath.

FIGS. 23 and 24 are front elevation views similar to FIGS. 20 and 21, except for the embodiment of FIG. 22, and with connection to the EP mapping system occurring directly through a proximal portion of the tube of the sheath.

FIG. 27 is a top plan view similar to that which is shown in FIG. 26, but after the base portion of the sheath has been separated from the tube portion of the sheath at the interface there between.

Figure 1:
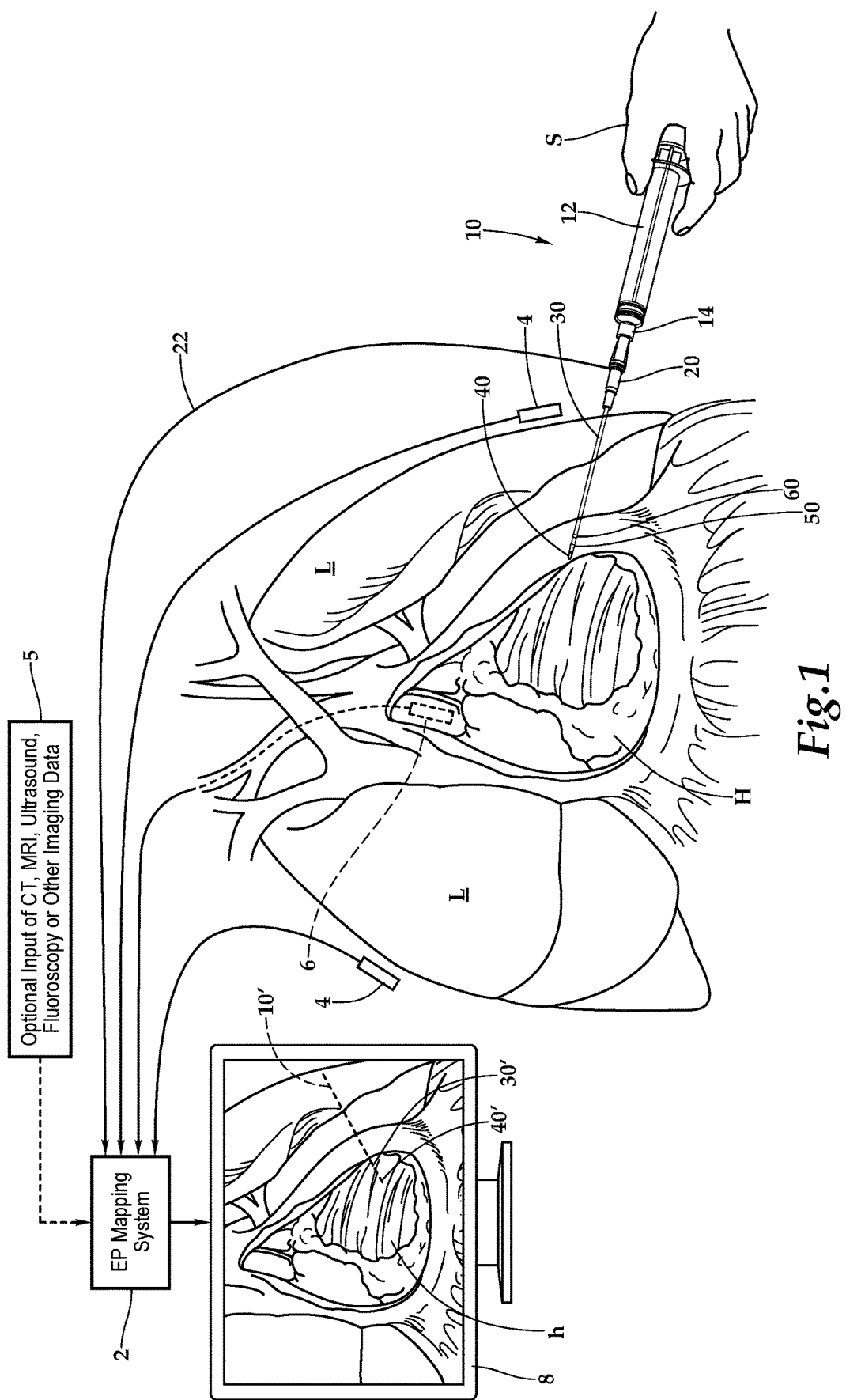
FIG. 1 is a schematic depiction of the system of this invention including a portion of a torso of a patient with a pericardiocentesis needle fitted with sensors in the form of electrodes shown engaging bodily structures proximate to the heart of a patient, and while the needle is visualized on a display of an EP mapping system, the EP mapping system relying primarily upon electrodes for generating the image displayed on the EP mapping system display.

FIG. 40 is a connector system for connecting navigation wires or stylets or other interventional devices in an interchangeable fashion to a common interface which then includes a cable extension to the EP mapping system, such that different devices can utilize a common interface to facilitate ease of swapping of interventional devices during a lead placement procedure.

FIG. 41 is a front elevation view of a guide wire fitted with multiple sensors according to a further embodiment of this invention.

FIG. 42 is a front elevation view of a dual wire navigation wire system with sensors thereon for location verification according to this invention.

FIG. 43 is a front elevation view of a dilator with sensors thereon and coupled to an EP mapping system according to this invention.

FIG. 44 is a front elevation view of a J wire fitted with sensors for use with an EP mapping system according to this invention.

FIGS. 45 through 47 are front elevation views of luminal catheters having various different sized curved tips and with different numbers and positions of sensors thereon, for use of the luminal catheters along with an EP mapping system according to this invention.

DESCRIPTION OF THE PREFERRED EMBODIMENT

Referring to the drawings, wherein like reference numerals represent like parts throughout the various drawing figures, reference numeral 910 is directed to an electrophysiology (EP) sheath (FIGS. 19 through 27) which provides one form of interventional device according to this invention. The sheath 910 provides support for a lead 960 to be routed to a particular desired location within or adjacent to a heart H of the patient. The sheath 910 includes sensors 950 thereon, such as in the form of electrodes or magnetic field sensors, which are coupled to an EP mapping system 2 (FIG. 18) which includes a display 8 which displays coronary structures as well as the sheath 910 (or other interventional structure) during the lead 960 placement procedure.

In particular, and with reference to FIGS. 19 through 27, basic details of the sheath 910 or described according to an exemplary embodiment. Other interventional devices utilizable with lead 960 placement are also generally described for use separately or in conjunction with the sheath 910. The sheath 910 includes a base 920 at a proximal end thereof. The base 920 supports an entrance 923 which can receive a lead 960 therein, as the lead 960 is threaded through the sheath 910. A tube 930 extends from the base 920, on a side thereof opposite the entrance 923 into the base 920. A stopcock assembly 940 can optionally be provided extending laterally from the base 920. A tube 930 extends from the base 920 on a side thereof opposite the entrance 923. The tube 930 provides a pathway along with the lead 960 can pass during placement of the lead 960 into a particular location within the heart H of a patient.

The tube 930 includes sensors 950 thereon, typically a plurality of such sensors 950 located along the tube 930. The sensors 950 can be electrodes or magnetic field sensors which are compatible with an EP mapping system 2 (FIG. 18), so that the tube 930 can be shown on a display 8 associated with the EP mapping system 2 adjacent to coronary structures adjacent to the heart H of a patient, along with other items such as a pericardiocentesis needle 10' having an electrode 30' adjacent to a tip 40'. The sheath 910 can have a variety of different configurations such as those depicted in FIGS. 19 through 27. Other interventional devices supporting lead placement can be visualized on an EP mapping system 2 by placing sensors, such as electrodes or magnetic field sensors thereon. Such other devices include exoskeletons 1010, stylets 1200, navigation wires 1400, dilators 1600, and luminal catheters 1800.

Another interventional device that can have sensors thereon to facilitate visualization within an EP mapping system 2 is a pericardiocentesis needle 10, such as that shown in FIGS. 1 through 17. Such a needle 10 (and other devices) are initially described in detail herein as background for the other interventional devices identified above.

Figure 2:
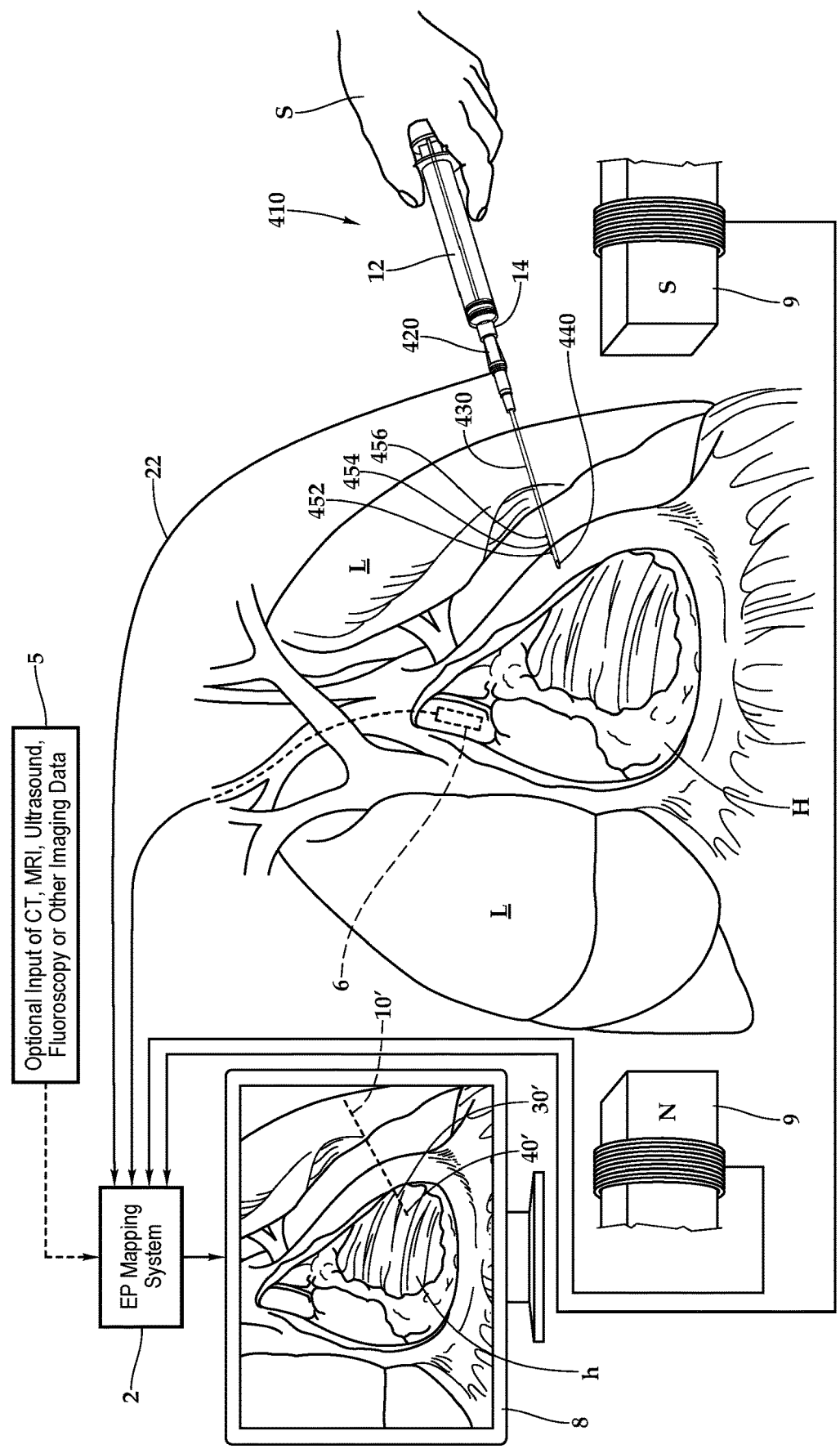
FIG. 2 is a schematic similar to that depicted in FIG. 1, but for an EP mapping system which primarily generates an image of cardiac structures based on placement of a magnetic field proximate to the patient and utilizing magnetic field sensors to localize the pericardiocentesis needle within the image displayed by the EP mapping system.

More specifically, and with particular reference to FIGS. 1 and 2, basic details of various EP mapping systems 2 are described, with which the needle 10 or other medical device of this invention is configured to interoperably perform. The EP mapping system 2 can be any of a variety of different medical visualization systems, but most preferably those which utilize electric and or magnetic fields to determine the location of bodily structures, and in this case, particularly cardiac structures of a patient.

As a general outline, the EP mapping system 2 can include a plurality of electrodes 4 in the form of surface electrodes on a surface of the patient. FIG. 1 depicts two such surface electrodes 4, but typically more than two such surface electrodes 4 would be utilized. Also, an intracardiac electrode 6 is typically also passed intravenously to a position within or adjacent to the heart H of the patient.

As explained in detail hereinabove, in one embodiment certain pairs of electrodes, such as the surface electrodes 4, switch between providing an excitation voltage resulting in the production of an electric field, and operating in a sensing mode wherever the electrodes sense voltage and/or current or other electrical properties at the locations of various electrodes. Together these electrodes, when switching between an excitation function and a sensing function, gather data about cardiac structures and other subcutaneous structures having different electrical properties, which data is converted into imagery suitable for presentation on the display 8 of the EP mapping system 2.

In one embodiment depicted in FIG. 2, the EP mapping system 2 either replaces the electrodes 4, 6 with magnetic field inducing elements such as magnets 9, or such magnetic field sources 9 augment an EP mapping system 2 which also includes electrodes 4, 6. Furthermore, cardiac structural data can be augmented with information from an auxiliary imaging source 5 and put into the EP mapping system 2. Such auxiliary input 5 can be provided from imaging devices such as computer tomography (CT), magnetic resonance imaging (MRI), ultrasound, fluoroscopy, or other imaging data.

Importantly with this invention, and as described below, the needle 10 or other transcutaneous medical device is fitted with electrodes 50, 60 or other sensors so that a position (and also preferably orientation) of the needle 10, and especially a tip 40 of the needle 10 can be visualized on the display 8 at an accurate position adjacent to heart H structures so that a position (and also preferably orientation) of the needle 10, and especially a tip 40 of the needle 10 can be visualized on the display 8 at an accurate position adjacent to the heart H and other bodily structures. On the display 8, the needle 10 appears as the needle 10' with the tip 40 appearing as a tip 40' and the shaft 30 of the needle 10 appearing as shaft 30'. A user, such as a surgeon S, can thus accurately position the needle 10 by viewing the display 8 of the EP mapping system 2 and moving the needle 10 to cause the tip 40 to be positioned where desired, while watching the display 8.

With continuing reference to FIG. 1, as well as FIG. 17, the needle 10 is described according to an initial exemplary embodiment. The needle 10 includes the hub 20 which supports the shaft 30 extending from the hub 20 to a tip 40. The hub 20 is configured to attach to other fluid handling structures, such as a syringe 12, such as through a luer fitting 14. The hub 20 also preferably has leads 22 which can extend to the EP mapping system 2, and which also connect to electrodes (or other sensors) on the needle 10. In this initial exemplary embodiment, the electrodes include a distal electrode 50 and a proximal electrode 60. By providing two electrodes 50, 60, when their position is determined a line segment between these two electrodes 50, 60 defines a central axis of the shaft 30 of the needle 10. Also, by knowing a distance that the tip 40 is spaced away from the distal electrode 50 (or other reference point), a position of the tip 40 can be precisely determined. This information can be superimposed into the imaging data set which is displayed in the display 8 of the EP mapping system 2, so that a needle 10', as well as a tip 40' of the shaft 30' can all be visualized (FIG. 1), even though no electrode is at the tip 40 of the needle 10.

While it is conceivable that the electrodes 50, 60 could have their own power supply and transmit signals associated therewith wirelessly to the EP mapping system 2, typically the electrodes 50, 60 are connected by a conducting wire 52, 62 from the electrodes 50, 60 through the leads 22 to the EP mapping system 2. FIG. 17 shows two such leads 22 which couple to the wires 52, 62 (FIG. 3) and which lead to the EP mapping system 2, such as along lead 22 (shown as a single line for convenience).

Figure 3:
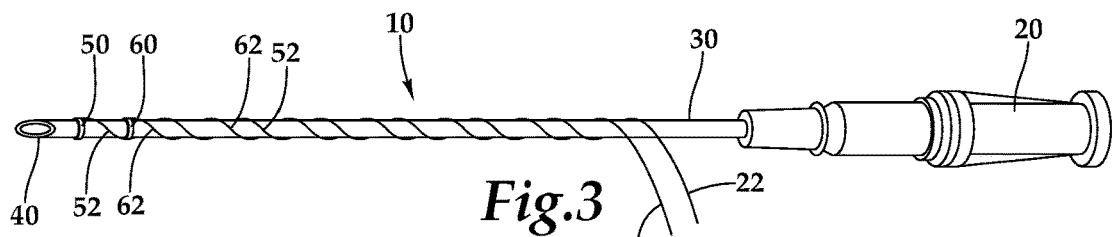
FIG. 3 is a perspective view of a pericardiocentesis needle according to a first embodiment of this invention.
Figure 5:
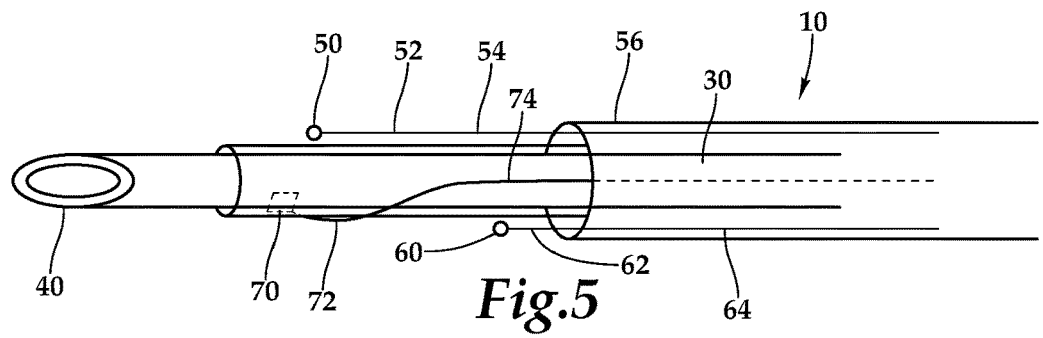
FIG. 5 is a detail of a portion of that which is shown in FIG. 3, and with electrodes shown schematically.

With particular reference to FIG. 3, a simplest form of the needle 10 with two electrodes 50, 60 coupleable to the EP mapping system 2 through external wires 52, 62 is disclosed. These wires 52, 62 are just left external to the shaft 30 of the needle 10 in this embodiment. Such an embodiment would typically perhaps only be used for testing, but could conceivably be utilized for therapeutic purposes. The wires 52, 62 might conceivably be left without any insulation jacket 54, 64 around the wires 52, 62, especially if the shaft 30 of the needle 10 is formed of a non-conducting material. However, typically these wires 52, 62 are encased within their own insulation jackets 54, 64 (FIG. 5). Also, these wires 52, 62 are preferably contained within an outer insulation 56 lining which holds the wires 52, 62 directly adjacent to the shaft 30.

Electrodes 50, 60 themselves could have any of a variety of different configurations, including configurations where they are flush with a surface of the shaft 30 of the needle 10, and embodiments where these electrodes 50, 60 extend outwardly, at least somewhat. In FIGS. 1-4, these electrodes 50, 60 are depicted as having a torroidal form and extending only very slightly away from the surface of the shaft 30. Most preferably, these electrodes 50, 60 are isolated from the shaft 30 of the needle 10 itself. For instance, and as depicted in FIG. 5, an inner lining of insulation can be provided directly adjacent to the shaft 30 of the needle 10. The electrodes 50, 60 are outboard of this innermost insulation lining. The wires 52, 62 are preferably provided with insulation jackets 54, 64 so that if these wires 52, 62 come into contact with each other, electric current is prevented from flowing therebetween. Finally, the outer insulation 56 is preferably provided to encase the wires 52, 62 and their associated insulation jackets 54, 64 are isolated from surrounding structures that the needle 10 might come in contact with. If the shaft 30 of the needle 10 is formed of non-conductive material, the innermost layer of insulation (FIG. 5) can be dispensed with.

The two electrodes 50, 60 are preferably provided a known distance apart from each other and with the distal electrode 50 a known distance away from the tip 40. For instance, the distal electrode 50 can be one inch away from the tip 40 and the proximal electrode 60 can be placed one inch away from the distal electrode 50. Such known distances between the electrodes 50, 60 and away from the tip 40 allow for accurate visualization of location and orientation of the tip 40 of the needle 10 on the display 8. As an example, if the shaft 30 of a needle 10 is extending along a central axis, with a proximal electrode 60 at an origin on the central axis, and the distal electrode 50 is at a one inch mark on this axis, it is known that the tip 40 will be at the two inch mark on this central axis. The coordinates of this central axis can be associated with what is fed to the display 8, and not only the positions of the electrodes 50, 60 can be provided, but also a virtual needle 10' can be animated and presented on the display 8, with the needle 10' extending right up to the tip 40'.

Bodily structures on the display 8 might hide the needle 10' at least somewhat. Known techniques with EP mapping systems 2 can be utilized to make sure that important structures can still be visualized. As one option, body structures "in front of" the portions of the needle 10' adjacent to the tip 40' can be cut away so that the tip 40' of the needle 10' can be seen. As another alternative, at least portions of the needle 10' can be shown in a phantom or broken line manner which perhaps becomes more pronounced or less pronounced based on a depth of the needle away from a view and perspective point, to represent depth. As another option, video editing tools can be utilized by a user to selectively remove bodily structures presented on the display 8 in a customizable fashion to display what the surgeon S or other medical practitioner wants to see, but remove enough detail so that important portions of the needle 10' can be clearly seen.

Figure 4:
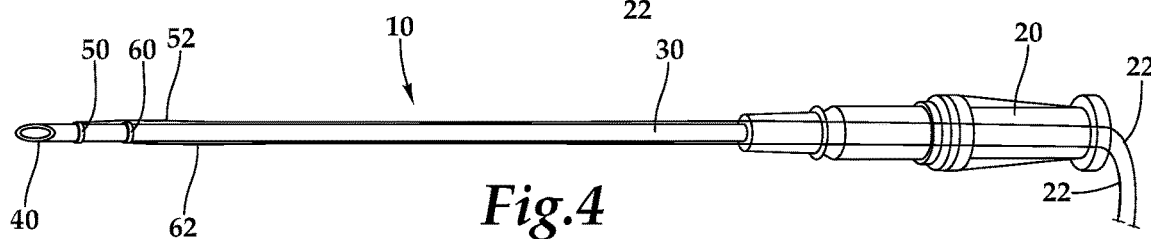
FIG. 4 is a perspective view of a modified version of that which is shown in FIG. 3.
Figure 6:
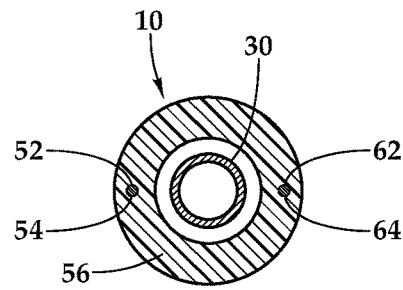
FIG. 6 is an end full sectional view of an embodiment of that which is shown in FIG. 3, which has both a proximal electrode and a distal electrode.

In FIG. 4 a variation of the needle 10 is displayed where the wires 52, 62 are held adjacent to the shaft 30, such as by placement inboard of outer insulation 56 (FIG. 5). The wires 52, 62 coupled to the electrodes 50, 60 are routed through the hub 20 in this embodiment, where they transition into the leads 22 extending to the EP mapping system. FIG. 5 further depicts, somewhat schematically, how different layers of insulation including innermost insulation and outer insulation 56 are located inboard and outboard of the electrodes 50, 60 and with the outer insulation 56 stopping short of positions for the electrodes 50, 60 so that the electrodes 50, 60 are not blocked from sensing electrical characteristics of bodily structures adjacent to the needle 10 and sensing the electric field sufficiently precisely to allow the electrodes 50, 60 to be located within a three-dimensional space adjacent to the heart H of a patient, without disruption by the electrically insulative character of the other insulation 56. Electrodes in FIG. 5 are seen schematically, rather than with any particular geometric configuration. FIG. 6 depicts how the wires 52, 62 and associated insulation jackets 54, 64 are located outboard of the shaft 30 but inboard of outer insulation 56 which is wrapped around an outer side of the wires 52, 62, or has the wires 52, 62 embedded within the outer insulation 56.

FIG. 5 also shows an optional additional sensor in the form of a force sensor 70. This force sensor 70 can be a strain gauge mounted to the shaft 30 of the needle 10, or some other force sensor 70. The force sensor 70 detects compression forces between the tip 40 and the hub 20. For instance, and especially when the tip 40 is large or less sharp, the tip 40 does not penetrate bodily tissues unless sufficient force is applied. In some instances, it is desirable to penetrate some tissues, but not others. For instance, when performing pericardiocentesis, the skin and surface anatomy, and the pericardium are penetrated, but one does not want to penetrate the myocardium. The force sensor transmits a signal, typically along a wire 72 inside of an insulation jacket 74 to the EP mapping system 2 or to a separate display of needle force. The signal can be calibrated and used to keep the tip 40 of the needle 10 from penetrating structures that require more force than a threshold amount, by having the surgeon S monitor the force sensed by the force sensor 70 and keeping it below the threshold maximum force.

Figure 7:
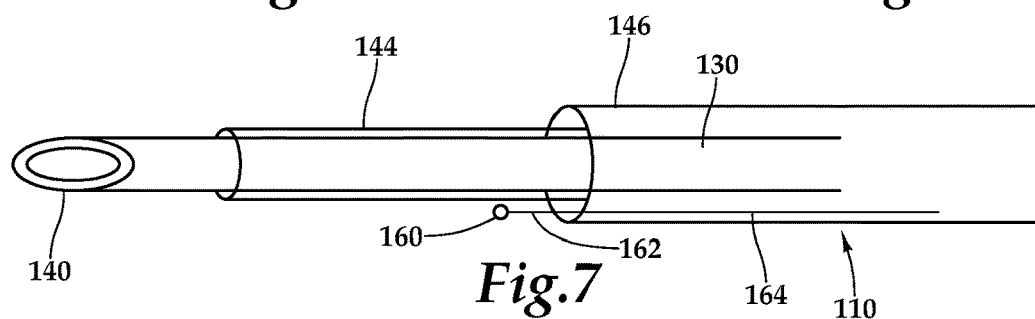
FIG. 7 is a perspective view of an embodiment of that which is shown in FIG. 3 which has a single electrode depicted schematically thereon, and where a tip of the needle can be an electrode.

With particular reference to FIG. 7, details of an alternative embodiment needle 110 are described. This alternative needle 110 is configured so that the tip 140 of the needle 110 can act as a distal electrode. The needle 110 includes a shaft 130 extending to the electrode tip 140. Shaft insulation 144 surrounds the shaft 130. Portions of the shaft 130 extending beyond the shaft insulation 144 generally act as an electrode. Preferably the shaft insulation 144 stops just short of the electrode tip 140, so that an approximation of a singular point can be associated with this electrode tip 140. Preferably in this embodiment, a proximal electrode 160 is also provided which is coupled to a wire 162 which preferably has its own insulation jacket 164. Outer insulation 146 can wrap around the wire 162 to hold the wire 162 adjacent to the shaft 130, but while preventing an electrical connection therebetween. The proximal electrode 160 would preferably be provided at a known distance away from the electric tip 140, so that the needle 110 would generally be effective in a manner similar to other multi-electrode needles such as the needle 10 (FIGS. 1-6).

Figure 9:
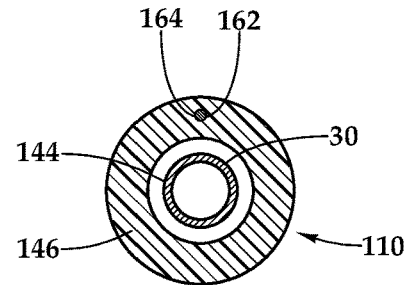
FIG. 9 is an end full sectional view of that which is shown in FIG. 7.

FIG. 9 depicts the embodiment of FIG. 7 in a full sectional end view, according to one embodiment where the wire 162 and insulation jacket 164 are embedded within the outer insulation 146, rather than merely having the outer insulation 46 wrapped outside of the wire 162.

Figure 8:
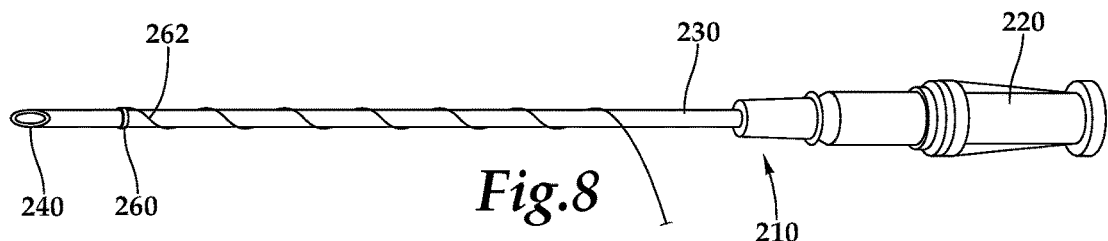
FIG. 8 is a perspective view of a modified version of that which is shown in FIG. 7.

FIG. 8 depicts a unipolar electrode needle 210. This unipolar electrode needle 210 includes a hub 220 with a shaft 230 of the needle 210 extending away from the hub 220 to a tip 240. A proximal electrode 260 is coupled to the shaft 230 a known distance away from the tip 240. A wire 262 extends from the proximal electrode 260 and is fed into the EP mapping system 2 (FIG. 1). Unipolar electrodes such as the proximal electrode 260 function by being coupled with some other electrode within the EP mapping system 2 or associated with some portion of the needle 210, or some other reference, so that meaningful information can be gathered with regard to the position (and preferably also orientation) of the needle 210.

In the embodiment depicted in FIG. 8, the wire 262 is merely wrapped around the exterior of the shaft 230, but could be covered with an outer insulation player, embedded within the shaft 230 or otherwise conveniently routed, or wiring could be dispensed with should be unipolar electrode 260 be fitted with a micro-mechanical power source of some form and a transmitter and other electronics to allow it to function as an electrode without an associated wire 262.

Figure 10:
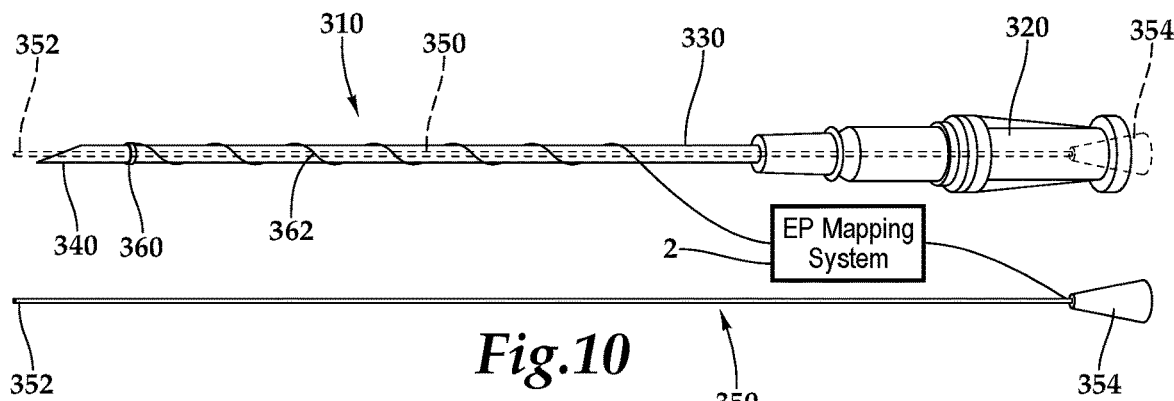
FIG. 10 is a perspective view of an embodiment of that which is shown in FIG. 3 where a single electrode is placed upon the needle and a stylet electrode is associated with the needle, the stylet electrode shown exterior to the needle and shown in broken lines placed within the needle.

With particular reference to FIG. 10, details of a needle/stylet 310 combination are described. In this embodiment, a hub 320 supports a shaft 330 extending out to a tip 340, similar to the needle 10 depicted in FIG. 3. However, only one electrode in the form of a proximal electrode 360 is provided on this shaft 330 spaced a known distance away from the tip 340. Wire 362 preferably extends from this proximal electrode 360 and is fed to the EP mapping system 2. A stylet 350 is also coupled to the EP mapping system 2 and has a distal end 352 opposite a base 354. The stylet 350 is preferably sufficiently long that the distal end 352 of the stylet 350 can pass entirely through a hollow center of the shaft 330 and extend out of the tip 340. The stylet 350 is preferably formed of electrically conductive material so that the distal end 352 can act as an electrode in this embodiment. As an alternative (or in addition), one or more magnetic field sensors can be placed on the stylet to convey its position (and preferably also orientation within the EP mapping system 2).

Preferably the shaft 330 is formed of electrically non-conductive material. As an alternative, the stylet 350 can have an outer insulative jacket formed of electrically non-conductive material or an interior of the shaft 330 can be coated with or otherwise lined with electrically non-conductive material. Between the distal end 352 of the stylet 350 and the proximal electrode 360, the combined needle/stylet 310 can function similar to a dual electrode needle such as that disclosed in FIGS. 1-6. The stylet 350 is movable relative to the shaft 330. The distal end 352 of the stylet 350 can be provided as a blunt tip, or with a sharpened tip, and with the tip 340 of the shaft 330 configured either to be sharp or somewhat blunted, so the various different functionalities can be provided between the shaft 330 and stylet 350 as is known in the stylet and needle arts as they pertain to cardiac surgery and related medical procedures and devices.

Figure 11:
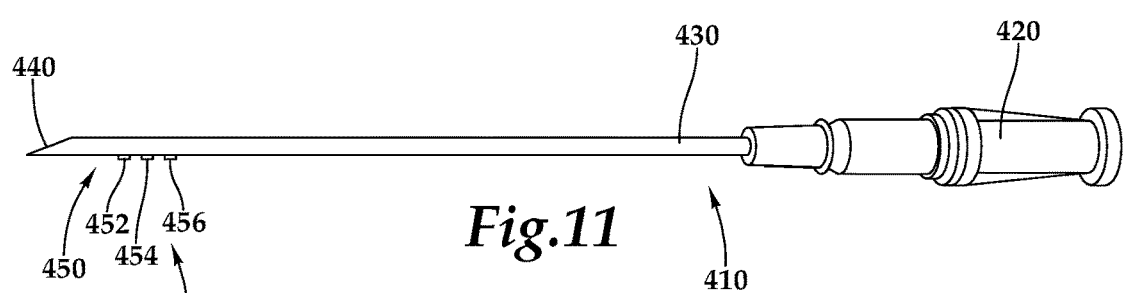
FIG. 11 is a perspective view of an embodiment of that which is shown in FIG. 3 which utilizes magnetic field sensors rather than electrodes, such as for use within the EP mapping system of FIG. 2.

With particular reference to FIG. 11, a needle 410 is disclosed which includes sensors which are preferably in the form of a magnetic field sensor set 450. The needle 410 includes a hub 420 upon which a shaft 430 is supported and extending out to a tip 440. The magnetic field sensor set 450 preferably includes three separate magnetic field sensors 452, 454, 456, such as sensors oriented in three mutually perpendicular orientations (e.g. X, Y and Z axes), so that the magnetic field from the sources 9 (FIG. 2) can be most accurately characterized at the location adjacent to this magnetic field sensor set 450. For simplicity, the sensors 452, 454, 456 are identified as boxes along a line, but could be oriented non-linearly and would most typically be solenoids or other coils with a generally cylindrical form.

Position (and preferably also orientation) can be ascertained based on a sensed intensity of the magnetic field relative to sources 9 (FIG. 2) of the magnetic field, and the position of bodily structures, and particularly cardiac structures which can be identified by electrodes, other magnetic sensors, other imaging systems, or combinations thereof. Thus, a position of the needle 410 fitted with the magnetic field sensor set 450 can be accurately determined and then displayed on the display 8 of the EP mapping system 2 (FIG. 2).

Figure 12:
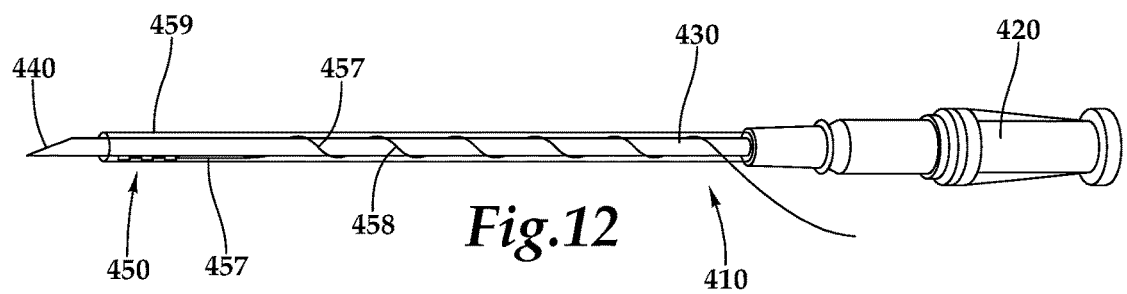
FIG. 12 is a perspective view of a modified version of that which is shown in FIG. 11.

Other details of the needle 410 are preferably similar to those disclosed above with respect to FIGS. 1 and 3-5. In this embodiment, for simplicity, no wires are shown, but typically, and as depicted in FIG. 12, the sensor set 450 would have at least one wire 457 extending therefrom (and optionally three wires in some embodiments) one to each individual sensor 452, 454, 456, and preferably with an insulation jacket 458 outboard of the wire 457 and within a jacket 459 surrounding the wires 457 and holding them adjacent to the shaft 430 of the needle 410, as depicted in FIG. 12, as one example.

Figure 13:
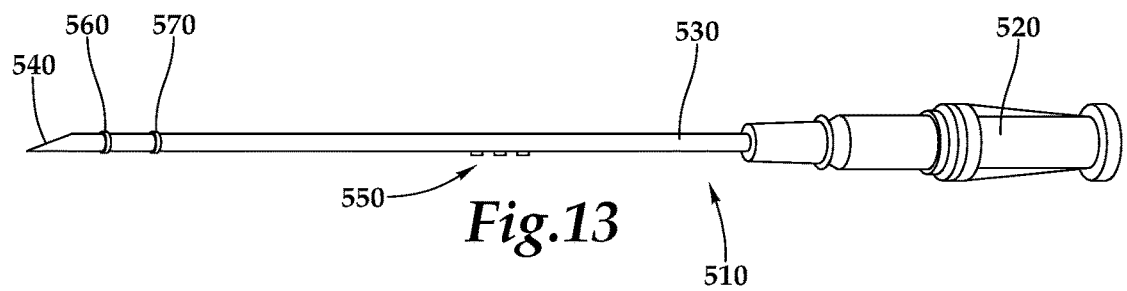
FIG. 13 is a perspective view of an alternative embodiment of that which is shown in FIG. 11 where the magnetic field sensors are located more proximal to a hub of the needle, and with optional electrodes are added to the needle so that a hybrid collection of magnetic field sensors and electrodes are provided together on a common needle, according to this embodiment.

With particular reference to FIG. 13, a hybrid needle 510 is disclosed that utilizes both magnetic field sensors 550 and at least one electrode 560, 570. In the embodiment depicted, a needle 510 includes a hub 520 with a shaft 530 extending therefrom to a tip 540. The shaft 530, includes a sensor, typically at any location thereon, but in the example depicted slightly closer to the hub 20 than to the tip 540, in the form of a magnetic field sensor set 550. Additionally, at least one electrode, and preferably both a distal electrode 560 and a proximal electrode 570 are also located upon the shaft 530. While wires are not depicted, they would typically extend from these sensors in the form of the magnetic field sensor set 550, as well as from the electrodes 560, 570. Information from the sensors is passed on to the EP mapping system 2 for most accurate visualization of the needle 510.

Figure 14:
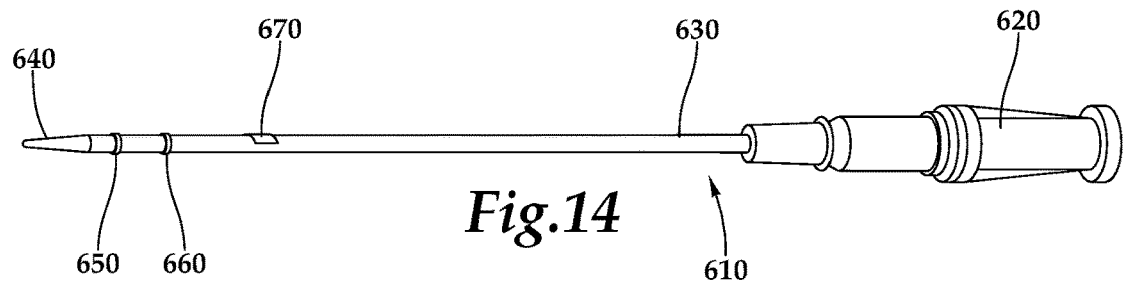
FIG. 14 is a perspective view of a dilator with electrodes thereon for visualization within an EP mapping system such as that disclosed in FIG. 1.

With particular reference to FIG. 14, an embodiment of this invention is depicted where a dilator 610 is fitted with electrodes 650, 660 as one form of sensor to allow for visualization of the dilator 610 within an EP mapping system 2. The dilator 610 includes a hub 620 with a shaft 630 extending therefrom to a tip 640. In this disclosed embodiment, two electrodes 650, 660 are coupled to the shaft 630 at known distances away from the tip 640. A force sensor 670 can also be provided. As one option, one of these electrodes 650 could be located at the tip 640. Typically wires extend from these electrodes 650, 660 and force sensor 670 and appropriate insulation is provided to keep these wires extending from the electrode 650, 660 from shorting out each other as they are routed back to the EP mapping system 2. With such a dilator 610, dilator placement can be most effectively controlled utilizing the EP mapping system 2, and particularly the display 8 thereof, to guide a surgeon S or other medical professional in the placing of the dilator 610 where desired.

With particular reference to FIGS. 15 and 16, two variations on a sheath, including a straight sheath 710 and a curved sheath 810 are disclosed. Shafts 730, 830 are either straight or curved, extending out to tips 740, 840. Hubs 720, 820 are provided opposite these tips 740, 840. With these sheaths 710, 810 valves 725, 825 are preferably provided at the hubs 720, 820 for placement of a dilator or other structure therethrough during a placement (also known as "introduction") procedure. Such devices are also referred to as introducers. A separate fluid control line typically interfaces with the hubs 720, 820, in the form of fluid manifolds 727, 827 to allow for fluid flow after placement of the sheaths 710, 810 where desired. Sensors, depicted in these embodiments as magnetic field sensor sets 750, 850 are provided upon the shafts 730, 830, and preferably adjacent to the tips 740, 840, which allow for a location of these sheaths, and particularly tips thereof, to be visualized through a display 8 of an EP mapping system 2 and for placement where desired. In addition to sheaths 710, 810 other medical devices can similarly be fitted with sensors to facilitate their viewing on a display 8 of an EP mapping system 2. Such other devices include catheters, scalpels, ablation tools, biopsy needles, shunts, drain tubes, etc.

While the magnetic field sensor or electrode (or set of two or more thereof, collectively considered as "the sensor") is shown attached to the needle body itself, in other embodiments the sensor could be on the hub of the needle or could be an accessory that is removably attachable to the needle. The accessory with the sensor can connect the needle to a syringe as an intermediate structure that acts as a syringe interface, or the accessory with the sensor can fit over the needle body itself. Similarly, the sensor could be within the syringe that is mounted on the needle. In each case, a cable would be routed back to the EP mapping system 2. The tip of the needle would be a known distance from this sensor and the EP mapping system 2 would display the needle in an accurate position and orientation by drawing the needle extending this known distance away from the actual position of the sensor on the hub, syringe or syringe interface.

Figure 18:
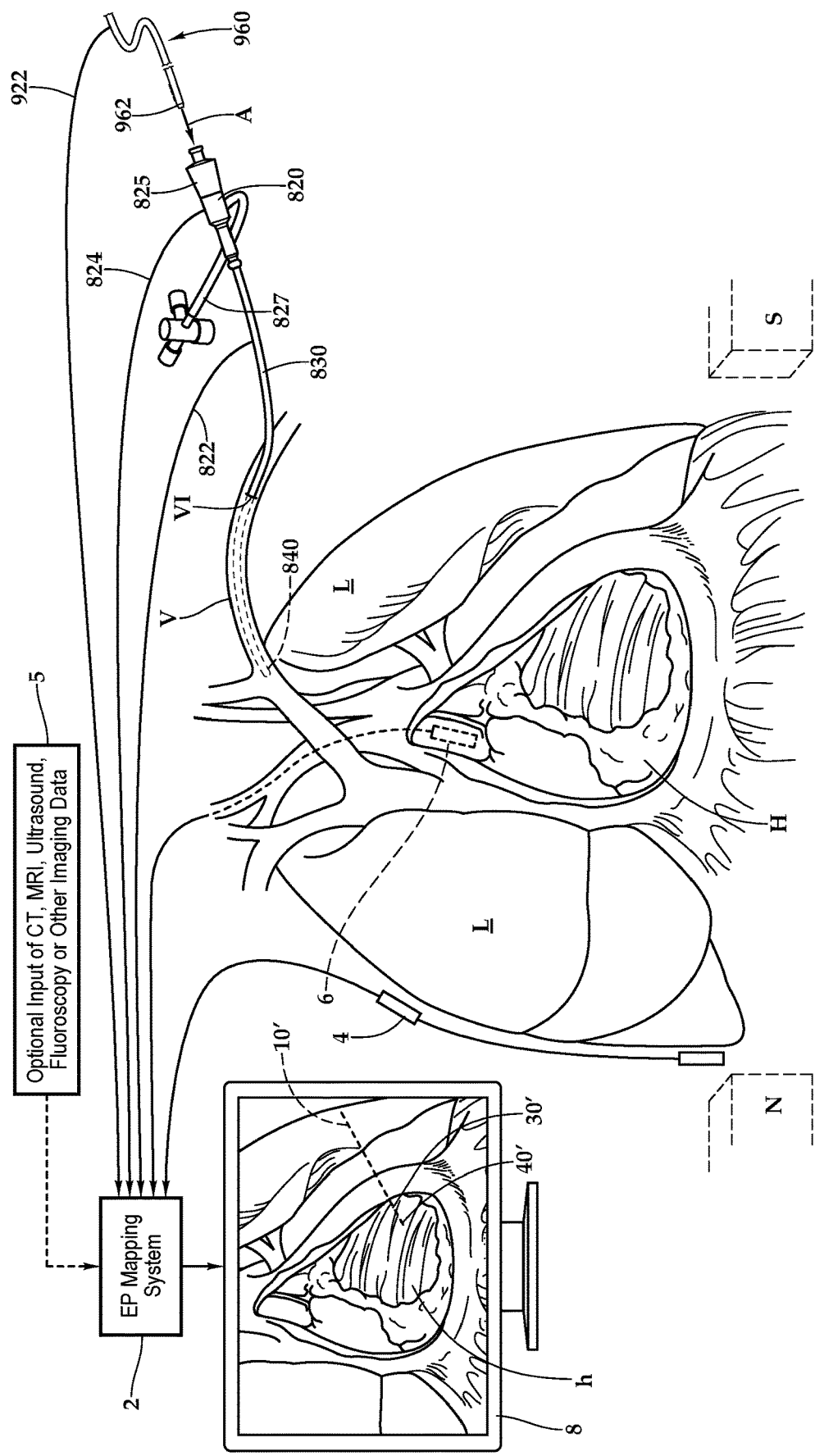
FIG. 18 is a schematic depiction similar to that which is shown in FIG. 1, but for a sheath passing into a subclavian vein, rather than for a pericardiocentesis needle.

With particular reference to FIG. 18, details of an EP mapping system 2 utilized during placement of a cardiac lead 960, such as a pacemaker lead, are described according to one embodiment which is exemplary of how the EP mapping system 2 can assist in coronary lead 960 placement. As depicted in FIG. 18, a subclavian vein V is utilized for accessing interior portions of the heart H for lead 960 placement. A sheath 810 is depicted with a tube 830 thereof passing through a vein incision VI and into the subclavian vein V. The sheath 810 also includes a base 820 with an entrance 825 through which the lead 960 can be placed. This sheath 810 also includes a stopcock subassembly 827 and a cable 824 or cable 822 which feed information to the EP mapping system 2 from sensors placed along the tube 830 of the sheath 810, either directly from the tube 830 along the cable 822 or through the base 820 along the cable 824.

The sheath 810 has the tube 830 thereof inserted into the subclavian vein V and then routed appropriately to a desired final location. Sensors on the tube 830 of the sheath 810 help to determine if it is located in the proper portion of the heart H. Either the lead 960 is already located within the sheath 810 during its placement, or the sheath 810 is first placed where desired, and then the lead 960 is routed through the sheath 810 (along arrow A of FIG. 18) to place the lead 960 were desired.

The lead 960 includes a lead tip 962 opposite a proximal end 964. The lead tip 962 is configured to deliver electric therapy to the heart, such as placing impulses. The proximal end 964 of the lead 960 (FIGS. 26 and 27) can be coupled to a pacemaker or intracardiac defibrillator (ICD) as a source of electric signal to be routed along the lead 960. Other approaches besides that through the subclavian vein V can alternatively be utilized with similar equipment.

With particular reference to FIGS. 19 through 27, an alternative EP sheath 910 to the sheath 810 depicted in FIG. 18 is disclosed in various different embodiments. A primary aspect of this EP sheath 910 is that the base 920 thereof can be separated from the tube 930 thereof, such as after placement or after a first portion of placement of the sheet 910 has occurred.

The sheath 910 includes a base 920 with the tube 930 extending in elongate fashion from the base 920. The base 920 includes an entrance 923 on one side thereof, opposite the tube 930. A fastener 924 is located within the base 920. This fastener 924 is configured to releasably clamp to the lead 960 so that the lead 960 can be held adjacent to the sheet 910, such as in an embodiment where the lead 960 is first placed through the sheath 910 before the sheath 910 is placed into a coronary pathway adjacent to the heart H of the patient, so that the sheath 910 is supporting the lead 960 during placement A cable 926 extends from this base 920 as well, in the embodiments depicted in FIGS. 19 through 21. In the embodiments of FIGS. 22 through 27 the cable 926 connects to a proximal terminus 934 of the tube at 930, separate from the base 920. The base 920 includes an interface 928 on the side of the base 920 adjacent to the tube 930. This interface 928 can be removably attached to the base 920 (along arrow B of FIGS. 20, 21, 23 and 24). Such removable attachability can be by configuring the interface 928 and base 920 to form two halves of a threaded pair, with one having male threads and the other having matching female threads, or can be configured as a clamp with the base 920 having a closed orientation clamping down on to the interface 928 and an open orientation where the interface 928 is released by the base 920. In one embodiment, the interface 928 merely has a friction fit with the base 920 and can be separated with appropriate tension force applied therebetween. Other forms of fasteners could alternatively do utilized.

Preferably, the interface 928 can be broken open to cause the tube 930 to be split longitudinally into at least two separate pieces. Such tearing open is depicted along arrow C of FIGS. 21 and 24. Such separation can facilitate removal of the tube 930 after placement of the lead 960 where desired.

The sensors 950 are located on the tube 930 most preferably with one sensor 950 adjacent to a distal tip 932 of the tube 930. A plurality of sensors 950 are provided, preferably with constant space therebetween, along the tube 930 and extending at least part of the way toward the proximal terminus 932 of the tube 930. Each of these sensors 950 is coupled via a wire 927 through the proximal terminus 934, along the cable 926, through a junction 929, and then as exposed individual wires terminating at connectors 925 which can be plugged into the EP mapping system 2. Other wire routing systems could alternatively be utilized. Each wire 927 typically involves an electrically conductive pathway which typically includes some form of insulation surrounding each conductive pathway.

Each sensor 950 can be either an electrode or a magnetic field sensor. The EP mapping system 2 can be of a variety which is based entirely upon electrodes and the establishment of an electric field in the chest cavity of the patient surrounding the heart H, or can be a combination of electrodes and magnetic field sensors, and with a magnetic field established surrounding a torso of the patient. Through differing electric and magnetic properties of the tissues within and surrounding the heart H of the patient, variable magnetic field strength and/or impedance, or other electric field measurement can be taken and correlated to coronary structures or other structures. These coronary structures and related structures can then be displayed on the display 8 of the EP mapping system 2. By placing sensors 950 on the tube 930, the tube 930 can also be visualized on this display 8 at proper location adjacent to other bodily structures. A surgeon or other medical professional can thus view the display 8 and see where the tube 930 of the sheath 910 (or other interventional device) is located, and, by watching the display 8 in real time, can place the lead 960 and/or other interventional device precisely where desired.

Figure 25:
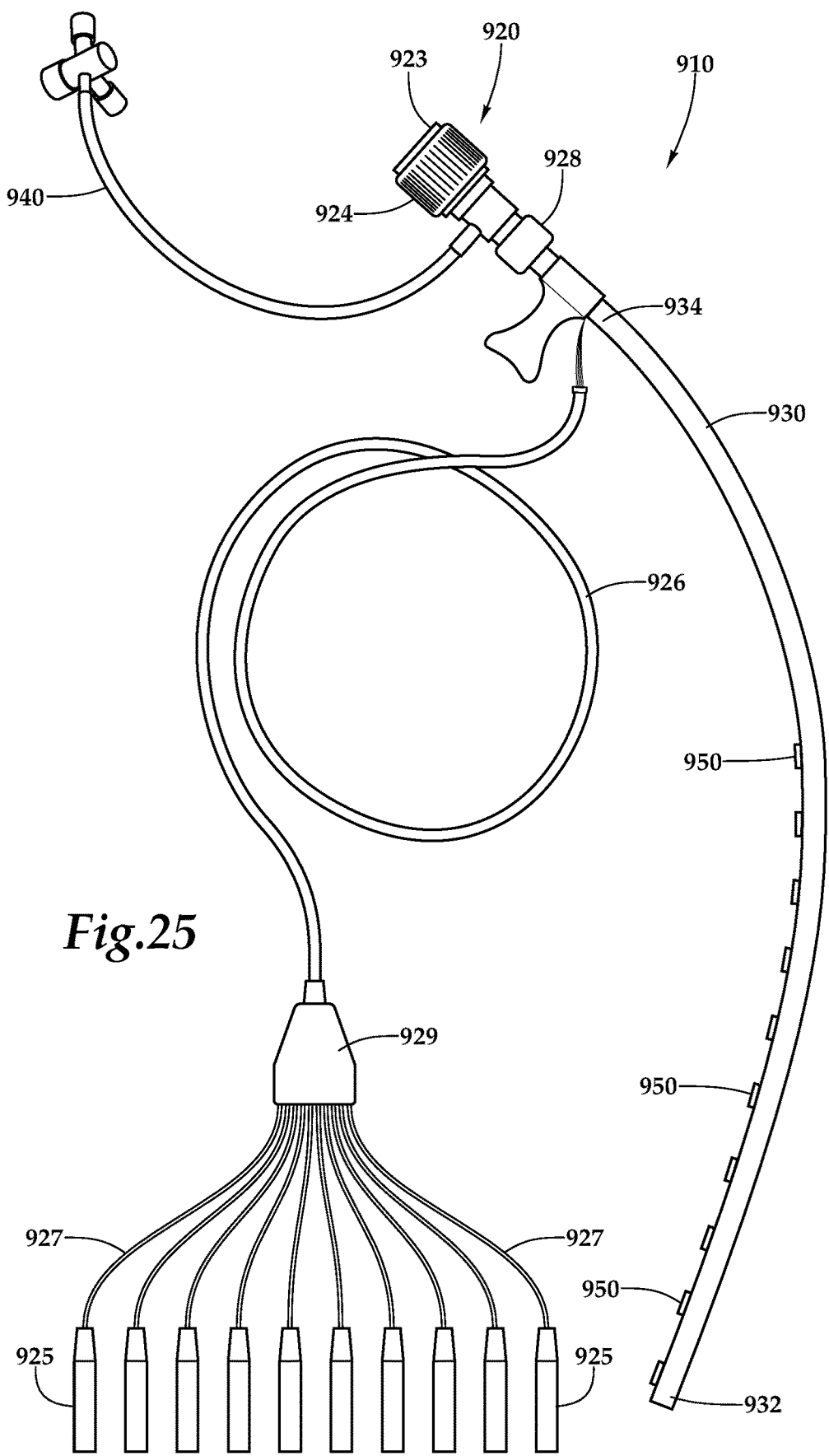
FIG. 25 is a top plan view of a sheath according to a further embodiment of this invention with details of a cable for interconnection to the EP mapping system and separation details at an interface between a base and a tube of the sheath.
Figure 26:
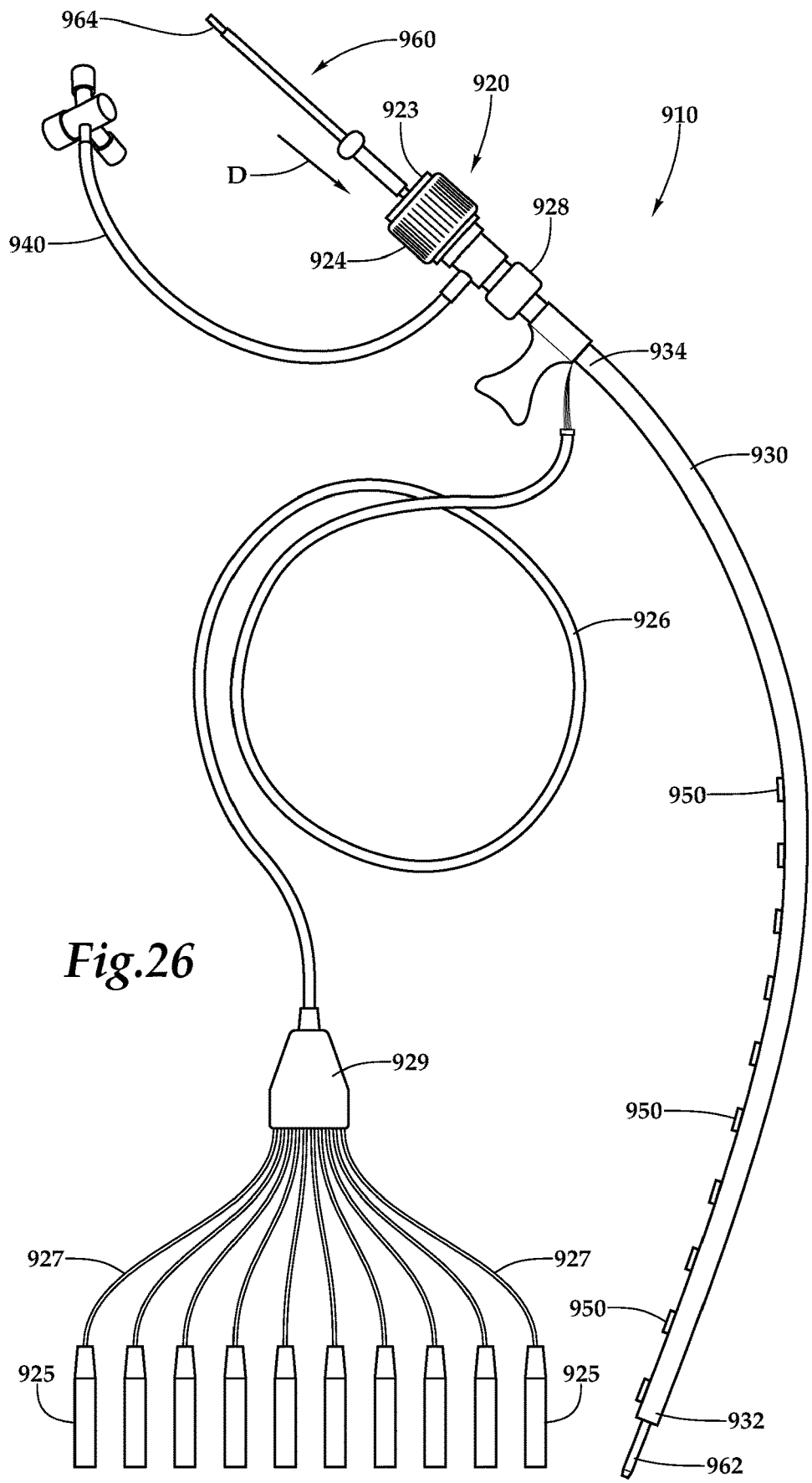
FIG. 26 is a top plan view similar to that which is shown in FIG. 25, but after a lead has been placed through the base and tube of the sheath.
Figure 27:
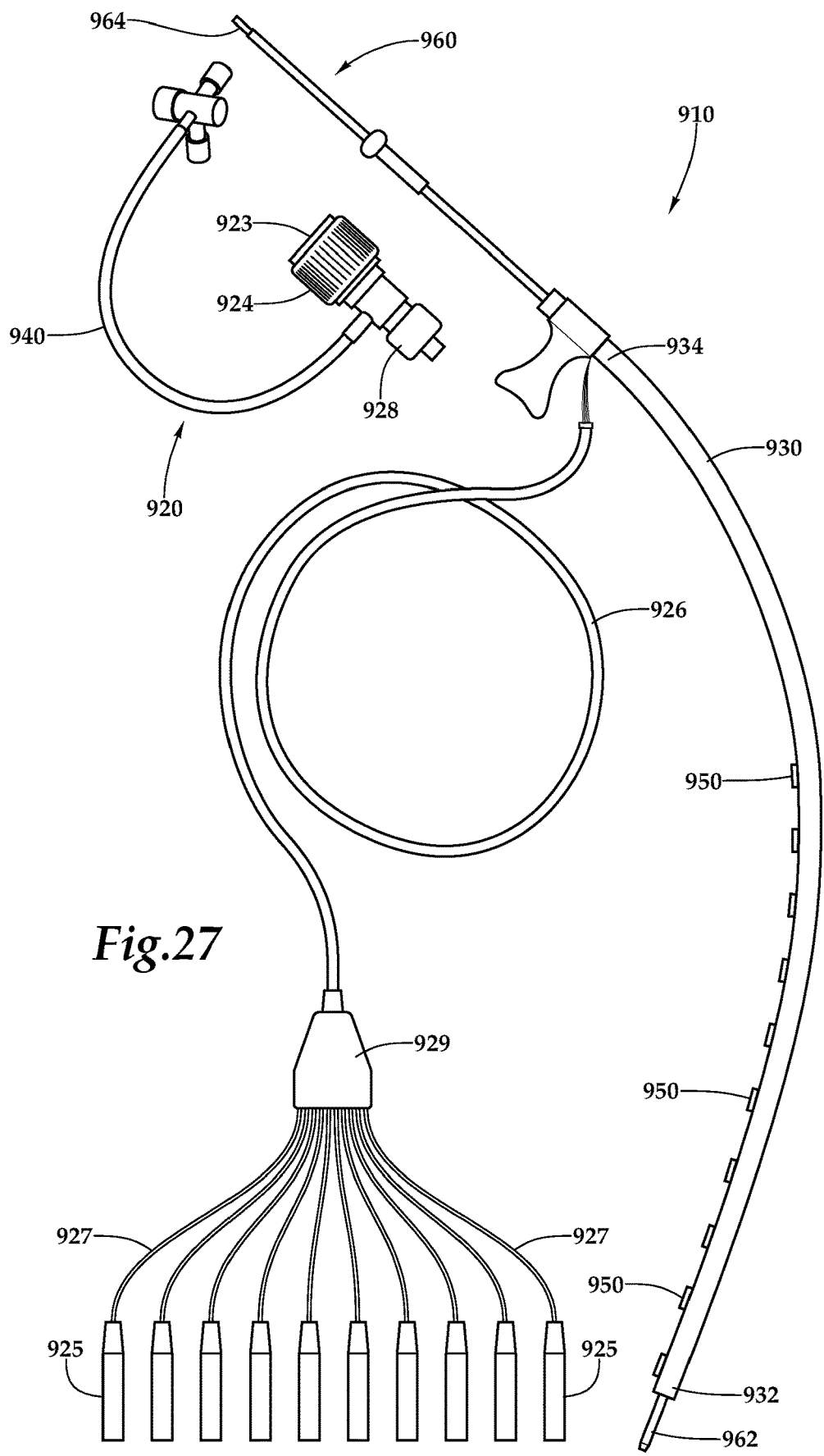

FIGS. 25 through 29 show a particular embodiment with ten sensors 950 along the tube 930. In FIG. 25, sheath 910 has not yet been loaded with the lead 960. In FIG. 26, the lead 960 has been routed (along arrow D) through the entrance 923 of the base 920, and then through the tube 930 and extending out the distal tip 932. In FIG. 27, the lead 960 is still in place within the sheath 910, but the base 920 and associated stopcock assembly 940 have been removed, leaving just the tube 930 upon the lead 960. The sensors 950 on the tube 930 identify the position of the lead 960.

With particular reference to FIGS. 28 through 33, various embodiments of an exoskeleton 1010 variation on the sheath 910 are described, according to an exemplary embodiment. The exoskeleton 1010 includes a base 1020 with the cable 1022 coupled thereto, and leading back to the EP mapping system 2. A spine 1030 extends in elongate fashion from the base 1020. The base 1020 can have an entrance passing therethrough, which allows the lead to pass through the base 1020, and the base 1020 can also act as a fastener to hold the lead tightly to the base 1020 after it has been routed through the base 1020. The spine 1030 has a series of splines 1040 extending laterally therefrom. These splines 1040 are formed of resilient material and can have the lead snapped between two fingers of each spline 1040.

Figure 28:
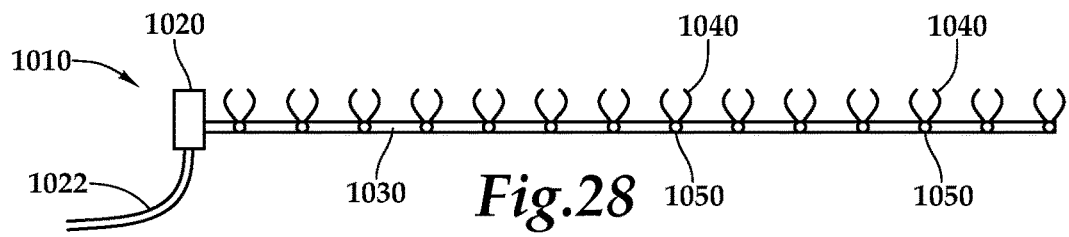
FIG. 28 is a front elevation view of an exoskeleton for attachment to a cardiac lead and for placement of EP mapping system sensors adjacent to the lead during placement within a cardiac space.
Figure 29:
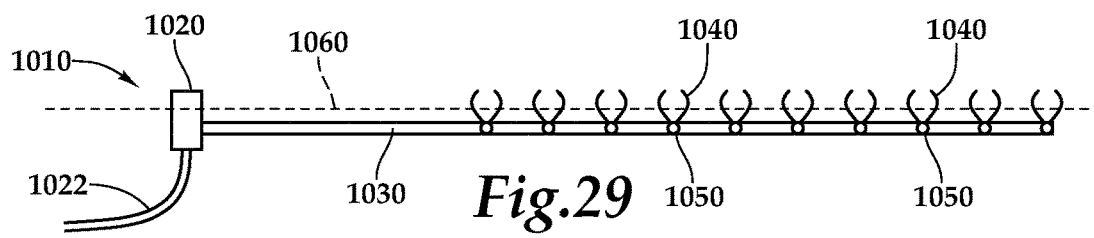
FIG. 29 is a front elevation view similar to that which is shown in FIG. 28, but with an optional additional spine of the exoskeleton shown in broken lines, and coupled to splines of the exoskeleton.

While the splines 1040 are shown with space therebetween maximized, they would typically be rotated 90° from that depicted, so that a widest spacing between fingers of the splines would be presented on either side of the lead after it passes through the entrance in the base 1020. Sensors 1050 are provided along the spine 1030. In the embodiment of FIG. 28, each spline 1040 also has a sensor 1050. In the embodiment of FIG. 29, the splines 1040 are concentrated near a distal end of the spine 1030, with one sensor 1050 for each spline 1040. Also in the embodiment of FIG. 29, a second optional spine 1060 (shown in broken lines) can be provided generally parallel with the main spine 1030. This second spine 1060 can also be attached to each of the splines 1040. Maneuvering the two spines 1060 in a differential fashion can cause the splines 1040 to more readily grip or release a lead passing through the splines 1040.

Figure 30:
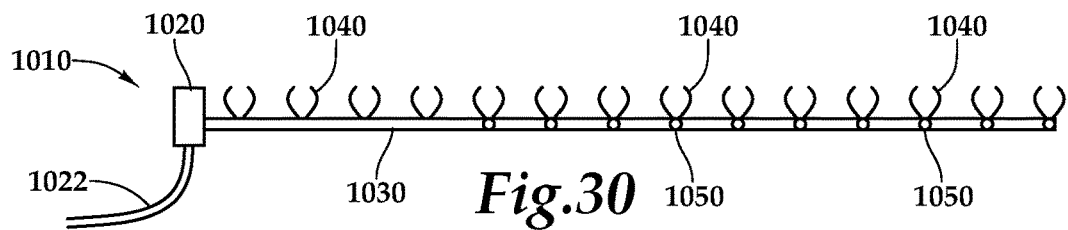
FIG. 30 is the front elevation view of the exoskeleton of FIG. 28, according to a modified embodiment with electrodes on only some of the splines.
Figure 31:
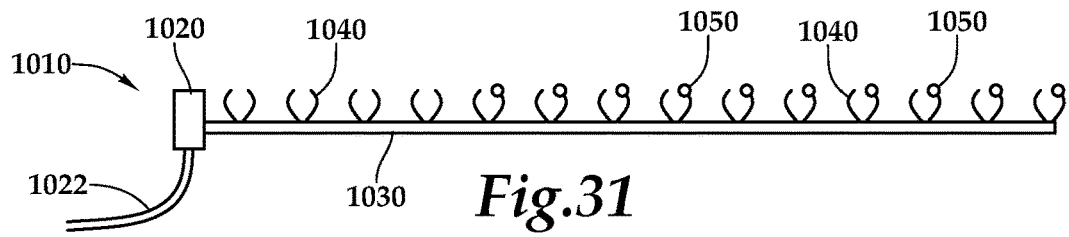
FIG. 31 is a front elevation view of an alternative embodiment of that was shown in FIG. 28, with the sensors located upon the splines rather than upon the spine.

In the embodiment of FIG. 30, the exoskeleton 1010 is shown with sensors 1050 on only some of the splines 1040. In the embodiment of FIG. 31, an exoskeleton 1010 is shown where the sensors 1050 are placed upon the splines 1040 rather than on the spine 1030, and only the splines 1040 closest to a distal end of the exoskeleton 1010 include the sensors 1050 thereon.

Figure 32:
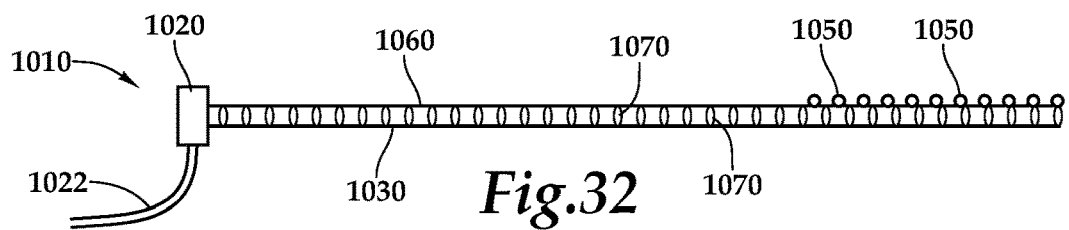
FIG. 32 is a front elevation view of an alternative embodiment of that which is shown in FIG. 28 with the splines replaced with thin wire loops which surround the lead during placement.

In the embodiment of FIG. 32, rather than having the splines 1040, a series of wire loops 1070 are provided. In this embodiment, a pair of spines 1030, 1060 are also provided, and the sensors 1050 are concentrated near a distal end of the exoskeleton 1010. Fine wires 1070 can be routed around the lead, such as during placement, and then the spines 1030, 1060 can be manipulated to remove the exoskeleton 1010 after the lead is placed where desired. Alternatively, the spines 1030, 1060 can be manipulated to cause the exoskeleton 1010 to tear apart, facilitating removal of the exoskeleton 1010.

Figure 33:
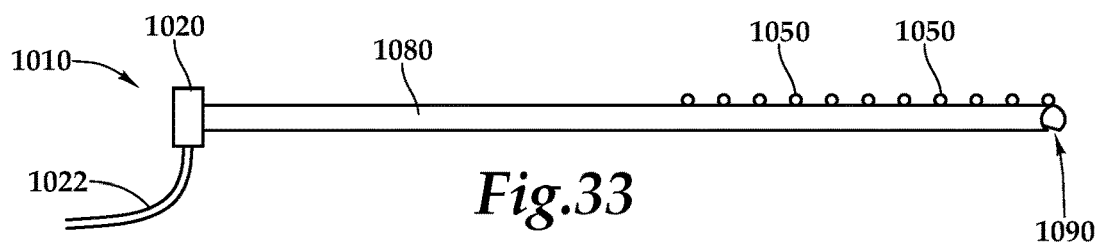
FIG. 33 is a front elevation view of an alternative embodiment of that which is shown in FIG. 28, in the form of a jacket with a slot having a continuous cross-sectional form, rather than the individual splines, and with sensors located upon this jacket.

In FIG. 33 an embodiment of exoskeleton 1010 is depicted where sensors 1050 are provided upon a generally tubular jacket 1080 which is open at a lower slot 1090 shown on an underside thereof. Such a jacket 1080 can be formed of resilient material and snapped onto the lead, or can have the lead snapped out of such a jacket when it is desired to move the lead out through the bottom slot 1090. In the embodiment depicted, the jacket 1080 circumscribes about ¾ of a circumference, so that the slot 1090 has a width similar to a diameter of the lead, with a slight friction fit as the lead snaps into and out of the jacket 1080 through the slot 1090.

Figure 34:
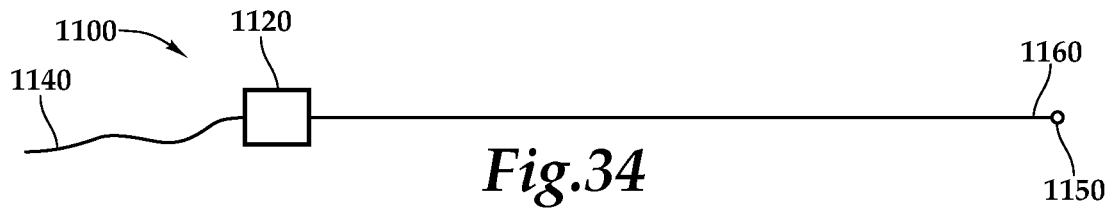
FIGS. 34 through 36 are front elevation views of a stylet for placement within other interventional devices, or navigation wires fitted with various arrays of sensors near distal tips thereof for visualization on the EP mapping system.
Figure 35:
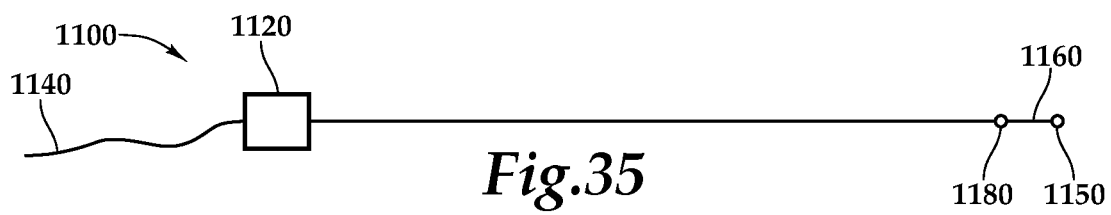
Figure 36:
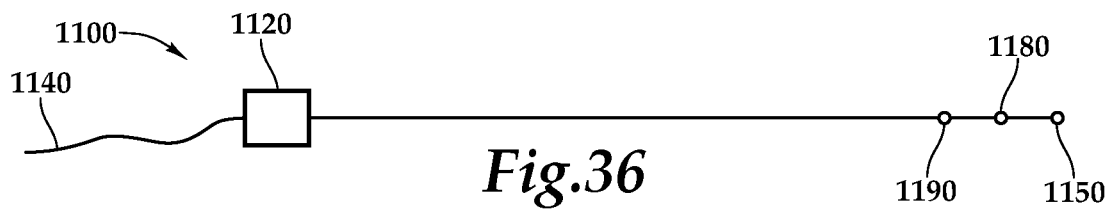

FIGS. 34 through 36 depict interventional devices in the form of thin elongate wires. These structures can either be navigation wires or stylets 1100. Stylets 1100 differ from navigation wires in that stylets 1100 are typically utilized through an interior of a tube, such as a catheter, tube of a sheath, lumen associated with a cardiac lead, or other tubular structure, while navigation wires are generally used separately without such a surrounding tubular structure.

The stylets 1100 each include a base 1120 with a cable 1140 extending from the base 1120 to an EP mapping system 2. The stylet itself extends from the base 1120 to a tip 1160. A sensor 1150 is provided at this tip 1160. In various embodiments, second sensor 1180 and/or third sensor 1190 can be provided. Sensors 1150, 1180, 1190 are preferably spaced a constant distance apart to allow for visualization of the location of the stylet 1100 with the EP mapping system 2.

Figure 37:
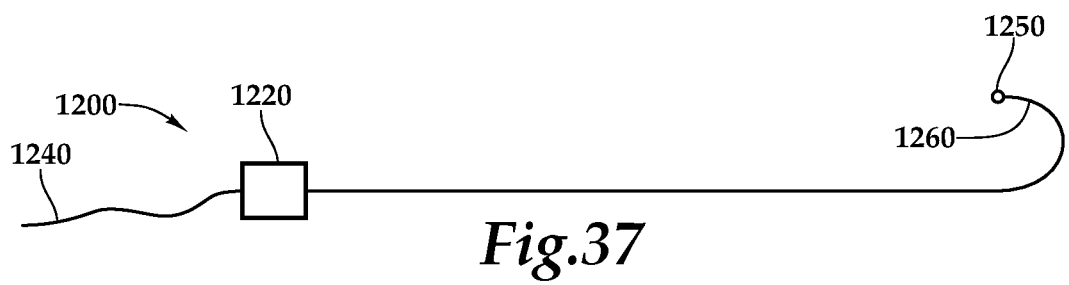
FIGS. 37 through 39 are front elevation views of stylets or navigation wires similar to those depicted in FIG. 34 through 36, but with a curved tip and with various different numbers of sensors located near a distal end of these curved tip navigation wires.
Figure 38:
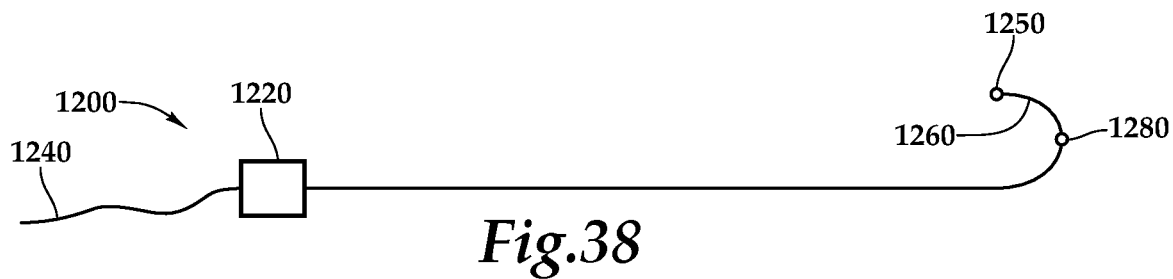
Figure 39:
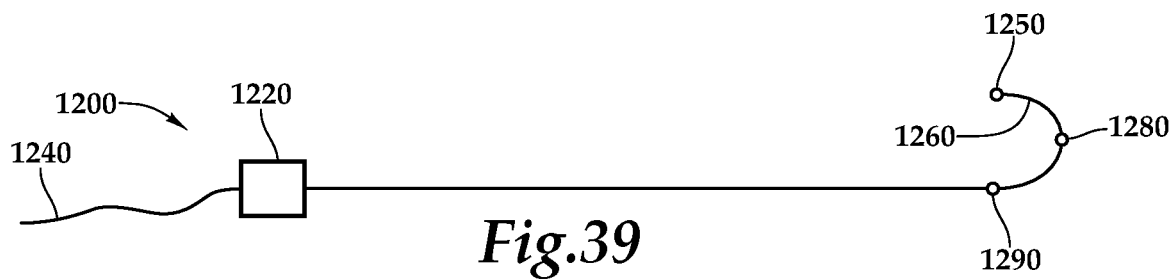

FIGS. 37 through 39 show further stylets 1200 which feature pre-formed curved tips 1260 on ends thereof opposite a base 1220. A cable 1240 extends from the base 1220 to the EP mapping system 2. The curved tip 1260 includes a sensor 1250 at a tip thereof. In related embodiments, a second sensor 1280 and third sensor 1290 can be provided at uniform spacing, and typically along the curve adjacent to the tip 1260. The curved tip 1260 of the curved stylet 1200 can thus be seen through the EP mapping system 2.

With particular reference to FIG. 40, details of a connector for a multiple interventional device support tool are described. An interface connector 1300 is provided with a cable 1340 leading to the EP mapping system 2. A stylet coupling 1350 is connected to this cable 1340, as well as to a clip 1370 which can be connected directly to a coronary lead. Various devices, such as base 1120 of a stylet 1110 can be coupled, such as along arrow E to the coupling 1350. Other interventional devices, such as sheaths, dilators, guide wires, J wire, or luminal catheters, which are fitted with electrodes, can alternatively be coupled, along arrow E, to the coupling 1350 of this interface 1300. A wire 1360 also extends to the stylet 1120 or other tool which is being connected.

With this removable interface 1300, it is not required that separate interventional devices be removed from and reattached to the EP mapping system 2 in an ad hoc fashion. Rather, the removable interface 1300 is wired to the EP mapping system 2, and each of the interventional devices, such as sheaths 910, exoskeletons 1010, stylets 1100,1200, guide wires 1400, dilators 1600 and catheters 1800 can be configured to plug into and out of the coupling 1350 of the removable interface 1300, for quick and easy substitution of the interventional devices through a common interface and common standard, so that the EP mapping system 2 does not require any special reconfiguring to switch from taking input from one interventional device to take input from another interventional device.

With particular reference to FIGS. 41 and 42 details of various guide wires with EP mapping are closed. In FIG. 41 a basic navigation wire 1400 is provided. A cable 1440 extends back to the EP mapping system 2. Sensors 1450 are provided on this navigation wire 1400 which can be visualized through the EP mapping system 2. The sensors 1450 are generally concentrated adjacent to the tip 1460, so that the tip 1460 in particular can have its location and orientation most effectively visualized.

In FIG. 42, a variation dual navigation wire 1500 is disclosed. In some instances, separate lead wires need to be routed to separate coronary structures, such as two different chambers in the heart H. With the guide wire 1500 a main wire body 1510 is fitted with sensors 1550. A secondary wire body is provided parallel with the main wire body 1510 which is connected by thin elements together to a sensor at a distal tip beyond the sensor 1550. Each wire is connected by a separate cable 1540, 1545 back to the EP mapping system 2. The main wire travels adjacent to the left ventricular lead while the second wire is with in the lumen of the left ventricular lead. The main wire houses the sensors while the secondary wire is very thin except at the opposite end which is stiffer to allow for back loading into the left ventricular lead. The entire double wire is been moved as a single unit to cannulate the desired coronary sinus branch. Once cannulated, the left ventricular lead is advanced over the secondary wire similar to a "buddy wire" technique. The thicker portion of the secondary wire is cut by the operator at the proximal end of the lead, and the main wire body is removed from the patient, along with the very thin secondary wire from the lumen of the left ventricular lead. This design allows for less space constraints for the magnetic sensor(s) or electrodes.

With particular reference to FIG. 44, details of a dilator 1600 are disclosed which include sensors thereon for use with an EP mapping system 2. The dilator 1600 includes a distal tip 1630 with multiple sensors 1650 adjacent to the tip 1630. A base 1610 is provided at a proximal end, with a cable 1620 extending to the EP mapping system 2. The dilator 1630 can in one embodiment have a central tunnel through which a guide wire can pass. in another embodiment, the dilator 1600 is configured to pass through an interior of a sheath such as the sheath 910, or through other catheters or tubular structures, all the while providing position for the dilator 1600 due to the sensors 1650 placed thereon, interacting with the EP mapping system 2.

In FIG. 44 a J wire 1700 is disclosed with a sharply curved distal end 1760 having at least one sensor 1750 thereon, and with at least one other sensor a known distance away from the sensor 1750 at the distal tip 1760. A cable 1720 extends from the J wire 1700, leading back to the EP mapping system 2. The EP mapping system 2 can thus display the position of the J-wire 1700 due to interaction of the sensors 1750 with the EP mapping system 2.

FIGS. 45 through 47 show three different variations of luminal catheters 1800 having distal tips 1860 having different curvatures associated there with. Multiple sensors 1850 are provided at this curving distal end 1860 of these different variations on the luminal catheters 1800. A cable 1820 connects to the liminal catheters 1800, which is electrically coupled to the sensors 1850 and leads back to the EP mapping system 2. The sensors 1850 allowe the luminal catheter 1800 to have at least it's curving tip visualized on the display 8 of the EP mapping system 2. Sensors 1850 could also be provided along other portions of the luminal cathethers 1800 for more complete visualization if desired.

The invention disclosed herein is further described in use, following this exemplary protocol:

1. Extrathoracic electrode or magnetic patches and magnet is placed around the patient based on cardiac electrophysiology mapping systems.

2. Cardiac and extra-cardiac structures can be visualized by multiple means and loaded into the cardiac electrophysiology mapping system without necessarily the need for placement of intracardiac catheters.

a) Transthoracic echo equipped with magnetic sensor or electrodes can visualize cardiac structures, blood vessels, and extracardiac structures, which can be interfaced with the cardiac electrophysiology mapping system. Details of such technology are described in the inventor's co-pending patent application Ser. No. 15/813,717, filed on Nov. 15, 2017, incorporated herein by reference in its entirety.

b) A posterior-anterior fluoroscopy image could be loaded into the cardiac electrophysiology mapping system. Since there are multiple fluoroscopic vendors, a common format could be utilized such as JPEG provided by the fluoroscopic system, or a camera can take a picture of the fluoroscopic video display, which can be downloaded into the mapping system. A PA view in the EP mapping system can be matched to the fluoroscopic image and can be "locked" into a PA map (where the angle of view cannot be changed on this particular map), and landmarks such as the clavicle and subxiphoid process can be used for reference. A reusable magnetic sensor can be placed at various reference locations to size the image to the locked view PA file. This would create a familiar image for the cardiac electrophysiologist to navigate the magnetic sensor mounted stylets in the pacing or ICD leads into the cardiac structure.

A Fluoroscopic image taken from a camera can be loaded into the mapping system. This view can be matched and locked into the mapping system. The fluoroscopic background gives the cardiac electrophysiologist a familiar visual reference, without needing to activate the fluoroscope. If a high quality camera is utilized, any fluoroscopic vendor could be used, and will be familiar to each individual operator. This technology exists in current mapping systems. If radiation exposure was of less concern, CT scan dicom file can be loaded and various land marks could be used to tag the subclavian vein, superior vena cava and concerned cardiac structures.

3. Venous access can be obtained with or without the assistance of the cardiac electrophysiology mapping system. The usual practice is to obtain venous with minimal or no use of fluoroscopy. A transthoracic echo equipped with a magnetic sensor/electrodes or CT scan can visualize salient venous structures for the cardiac electrophysiology mapping system. A magnetic sensor or electrode mounted needle could be used to directly visualize the entrance of the needle into the intravascular space using the cardiac electrophysiology mapping system. Venous access can be confirmed with the magnetic sensor J wire, or a traditional J wire using fluoroscopy can be utilized. A dilator and sheath is placed over the J wire which can be equipped with a magnetic sensor or electrodes. However standard sheaths could also be utilized.

4. Permanent pacing leads or defibrillators leads with magnetic sensor mounted stylet, with electrodes connected to the mapping system could be directly visualized as it travels through the vascular tree and navigated to various locations in the right atria or right ventricle.

5. The stylets can be shaped and replaced to steer the permanent pacing/ICD lead to the desired location which is visualized using the cardiac electrophysiology mapping system.

6. Once leads are in place, leads are deployed, and stylets are removed. Standard technique is used to secure the device and leads.

7. For placement of a coronary sinus lead:
    a) Once vascular access obtained, a standard EP catheter can be used to cannulate the coronary sinus. This could also be a catheter equipped with a magnetic sensor (but without ablation capabilities) to establish a matrix around the coronary sinus.
    b) Sheath with magnetic sensor or electrodes are placed over the EP catheter and into the coronary sinus.
    c) Usual practice is to visualize the coronary sinus tree by injecting radiocontrast into the sheath under fluoroscopy. Using the standard left anterior oblique view of the heart, branch vessels of the coronary sinus can be visualized. A JPEG file can be made of the desired image, and transferred to the EP mapping system either by direct communication or by a high resolution camera. The matching view in the electrophysiology mapping system and the fluoroscopic image can be "locked" together into a map (where the angle of view cannot be changed on this particular map). Sizing can be used by calibrating the EP catheter and coronary sinus sheath to the fluoroscopic image. Standard EP catheters, magnetic sensor mounted sheaths, luminal catheters, magnetic sensor mounted stylets within permanent leads and magnetic sensor mounted coronary sinus wires could be visualized on this "locked" two dimensional map in the cardiac electrophysiology mapping system with the background of the fluoroscopic image An image of a catheter within the coronary sinus can be imported into a cardiac electrophysiology mapping system, and this view locked in place. This allows for the coronary sinus wire to be fed into the selected branch without the need for active fluoroscopy. A coronary sinus catheter is visualized in place which can have mounted electrodes or magnetic sensor, which will show the location of the tip as it is maneuvered within the coronary sinus in the EP mapping system, with the locked image as a background. A coronary sinus wire mounted with an electrode or magnetic sensor is also visualized on the EP mapping system with the locked image as a background. The left ventricular lead is visualized since the electrodes are also visualized by the EP mapping system.

i. Luminal catheter with magnetic sensor or electrodes can subselect a desired branch using the cardiac electrophysiology mapping system.

ii. Desired branch is cannulated with the magnetic sensor mounted coronary sinus wire.

iii. Left ventricular pacing lead is placed over the coronary sinus magnetic sensor mounted wire and into the desired coronary sinus branch. All sheaths and coronary sinus wire removed from the patient by a slitter, which can be oriented to run parallel with the coronary sinus sheath. Coronary sinus pacing lead secured using standard techniques.

For "leadless" pacemakers, which are placed by the femoral vein, A catheter mounted with either electrodes or magnetic sensor can be utilized to visualize the location of the catheter using a cardiac electrophysiology mapping system.

This disclosure is provided to reveal a preferred embodiment of the invention and a best mode for practicing the invention. Having thus described the invention in this way, it should be apparent that various different modifications can be made to the preferred embodiment without departing from the scope and spirit of this invention disclosure. When structures are identified as a means to perform a function, the identification is intended to include all structures which can perform the function specified. When structures of this invention are identified as being coupled together, such language should be interpreted broadly to include the structures being coupled directly together or coupled together through intervening structures. Such coupling could be permanent or temporary and either in a rigid fashion or in a fashion which allows pivoting, sliding or other relative motion while still providing some form of attachment, unless specifically restricted.

What is claimed is:

1. A system for supporting placement of a cardiac lead at a particular desired location in a patient's heart, the system comprising in combination:
    an electrophysiology mapping system including a display and a plurality of mapping system sensors, said mapping system sensors coupled to said mapping system and producing an image on said display indicative of subcutaneous structures of a patient;
    a sheath including a base, a tube extending from said base to a distal tip, and an entrance into said tube through said base; and
    a plurality of tube sensors upon said tube of said sheath, said tube sensors coupled to said EP mapping system to cause the tube to be visible on said display of said EP mapping system.

2. The system of claim 1 wherein said base includes a lead fixation clamp thereon for selectively holding and releasing a portion of a cardiac lead by said base of said sheath.

3. The system of claim 1 wherein a cable extends from said EP mapping system to said base of said sheath, said cable further electrically coupled to said plurality of tube sensors.

4. The system of claim 1 wherein a separable junction is located at an interface between said base and a proximal portion of said tube, for separating said tube from said base.

5. The system of claim 4 wherein a cable extends from said EP mapping system to said proximal portion of said tube, said cable further electrically coupled to said plurality of tube sensors.

6. The system of claim 5 wherein said cable includes a multi wire bundle with a separate wire for each of said plurality of tube sensors, each said wire also including a separate connector for connecting to the EP mapping system.

7. The system of claim 6 wherein said plurality of tube sensors includes at least one magnetic field sensor, and wherein said EP mapping system includes a magnetic field placed proximal to a cardiac space of a patient.

8. The system of claim 6 wherein said plurality of tube sensors includes a plurality of electrodes.

9. The system of claim 4 wherein said separable junction includes two halves of a threaded pair, with one of said halves having male threads and another of said halves having female threads matching said male threads.

10. The system of claim 4 wherein said separable junction includes a clamp on said base and a flange on said proximal portion of said tube, said clamp releasably engaging said flange.

11. The system of claim 4 wherein said separable junction includes said proximal portion having a friction fit into said base, with said proximal portion removable from said base by applying a force greater than friction between said proximal portion and said base.

* * * * *